(12) United States Patent
Harding

(10) Patent No.: US 7,499,523 B2
(45) Date of Patent: Mar. 3, 2009

(54) SYSTEMS AND METHODS FOR IDENTIFYING A SUBSTANCE

(75) Inventor: Geoffrey Harding, Hamburg (DE)

(73) Assignee: General Electric Company, Schenectady, NY (US)

( * ) Notice: Subject to any disclaimer, the term of this patent is extended or adjusted under 35 U.S.C. 154(b) by 197 days.

(21) Appl. No.: 11/498,113

(22) Filed: Aug. 2, 2006

(65) Prior Publication Data

US 2009/0028294 A1    Jan. 29, 2009

(51) Int. Cl.
    *G01B 15/00* (2006.01)
(52) U.S. Cl. .......................................... 378/90; 378/86
(58) Field of Classification Search ............. 378/88–89, 378/70, 82, 83
    See application file for complete search history.

(56) References Cited

U.S. PATENT DOCUMENTS

| | | | |
|---|---|---|---|
| 4,514,691 A | 4/1985 | De Los Santos et al. | |
| 5,044,002 A | 8/1991 | Stein | |
| 5,078,952 A | 1/1992 | Gozani et al. | |
| 5,115,459 A | 5/1992 | Bertozzi | |
| 5,153,439 A | 10/1992 | Gozani et al. | |
| 5,251,240 A | 10/1993 | Grodzins | |
| 5,420,905 A | 5/1995 | Bertozzi | |
| 6,088,423 A | 7/2000 | Krug et al. | |
| 6,424,695 B1 * | 7/2002 | Grodzins et al. | 378/87 |
| 6,532,276 B1 | 3/2003 | Hartick et al. | |
| 6,754,304 B1 * | 6/2004 | Kumakhov | 378/45 |
| 7,046,761 B2 | 5/2006 | Ellenbogen et al. | |
| 7,132,942 B1 | 11/2006 | Buess et al. | |
| 2008/0037707 A1 * | 2/2008 | Rothschild et al. | 378/57 |

OTHER PUBLICATIONS

U.S. Appl. No. 11/434,431, filed May 15, 2006, Geoffrey Harding.
U.S. Appl. No. 11/504,263, filed Aug. 15, 2007, Geoffrey Harding.
U.S. Appl. No. 11/498,114, filed Aug. 2, 2006, Geoffrey Harding.
U.S. Appl. No. 11/484,186, filed Jul. 11, 2006, Geoffrey Harding.
U.S. Appl. No. 11/416,526, filed May 3, 2006, Geoffrey Harding et al.
U.S. Appl. No. 11/541,716, filed Sep. 29, 2006, Geoffrey Harding.
U.S. Appl. No. 11/531,019, filed Sep. 12, 2006, Geoffrey Harding.
U.S. Appl. No. 11/434,486, filed May 15, 2006, Geoffrey Harding.
U.S. Appl. No. 11/434,291, filed May 15, 2006, Geoffrey Harding.
U.S. Appl. No. 11/504,395, filed Aug. 15, 2006, Geoffrey Harding.
U.S. Appl. No. 11/531,037, filed Sep. 12, 2006, Geoffrey Harding.

(Continued)

*Primary Examiner*—Hoon Song
(74) *Attorney, Agent, or Firm*—Eugene Hyun, Esq.; Armstrong Teasdale LLP

(57) ABSTRACT

A method for identifying a substance is described. The method includes detecting, by a first scatter detector, a first set of scattered radiation, generating a first effective atomic number from the first set of scattered radiation, detecting, by a second scatter detector, a second set of scattered radiation, generating a second effective atomic number from the second set of scattered radiation, and determining whether the first effective atomic number is within a limit of the second effective atomic number.

19 Claims, 20 Drawing Sheets

OTHER PUBLICATIONS

Hubbell, J.H., Veigele, W.J., Briggs, E.A., Brown, R.T., Cromer, D.T., Howerton, R.J., "Atomic Form Factors, Incoherent Scattering Functions and Photon Scattering Cross-sections," Journal of Physics and Chemical Reference Data, vol. 4, No. 3, pp. 471-538 (1975).

Hubbell, J.H., Veigele, W.J., Briggs, E.A., Brown, R.T., Cromer, D.T., Howerton, R.J., "Erratum; Atomic Form Factors, Incoherent Scattering Functions, and Photon Scattering Cross Sections," Journal of Physics and Chemical Reference Data, vol. 6, pp. 615-616 (1977).

Schlomka et al., "Coherent Scatter Computer Tomography—A Novel Medical Imaging Technique," Physics of Medical Imaging, Proceedings of SPIE—vol. 5030, pp. 256-265 (2003).

Rabiej M., "Determination of the Degree of Crystallinity of Semicrystalline Polymers by Means of the 'OptiFit' Computer Software," Polimery 6, pp. 423-427 (2002).

"Percentage Crystallinity Determination by X-Ray Diffraction," XRD-6000 Application Brief, Kratos Analytical—A Shimadzu Group Company, pp. 1-5 (1999).

A.M. Hindeleh and D. J. Johnson, "The Resolution of Multipeak Data in Fibre Science," J. Phys. D: Appl. Phys., vol. 4. Printed in Great Britain, pp. 259-263 (1971).

* cited by examiner

SYSTEMS AND METHODS FOR IDENTIFYING A SUBSTANCE

BACKGROUND OF THE INVENTION

This invention relates generally to imaging systems and more particularly to systems and methods for identifying a substance.

The events of Sep. 11, 2001 instigated an urgency for more effective and stringent screening of airport baggage. The urgency for security expanded from an inspection of carry-on bags for knives and guns to a complete inspection of checked bags for a range of hazards with particular emphasis upon concealed explosives. X-ray imaging is a widespread technology currently employed for screening. However, it is difficult for existing x-ray baggage scanners, including computed tomography (CT) systems, designed for detection of explosive and illegal substances to validate a plurality of parameters or characteristics of the substances.

A plurality of identification systems based on a plurality of x-ray diffraction (XRD) techniques provide an improved discrimination of materials compared to that provided by the x-ray baggage scanners. The XRD identification systems measure a plurality of d-spacings between a plurality of lattice planes of micro-crystals in materials. However, it is difficult for the XRD identification systems to validate the parameters of the materials.

BRIEF DESCRIPTION OF THE INVENTION

In one aspect, a method for identifying a substance is described. The method includes detecting, by a first scatter detector, a first set of scattered radiation, generating a first effective atomic number from the first set of scattered radiation, detecting, by a second scatter detector, a second set of scattered radiation, generating a second effective atomic number from the second set of scattered radiation, and determining whether the first effective atomic number is within a limit of the second effective atomic number.

In another aspect, a system for identifying a substance is described. The system includes a first scatter detector configured to detect a first set of scattered radiation and a second scatter detector configured to detect a second set of scattered radiation. The system further includes a processor configured to generate a first effective atomic number from the first set of scattered radiation, to generate a second effective atomic number from the second set of scattered radiation, and to determine whether the first effective atomic number is within a limit of the second effective atomic number.

In yet another aspect, a system for identifying a substance is described. The system includes a plurality of x-ray sources configured to generate x-rays, a first scatter detector configured to detect a first set of scattered radiation generated from the x-rays, a second scatter detector configured to detect a second set of scattered radiation, a processor, and a plurality of switches configured to couple the processor to the first set of scattered radiation when decoupling the processor from the set second of scattered radiation.

DETAILED DESCRIPTION OF THE INVENTION

Figure 1:
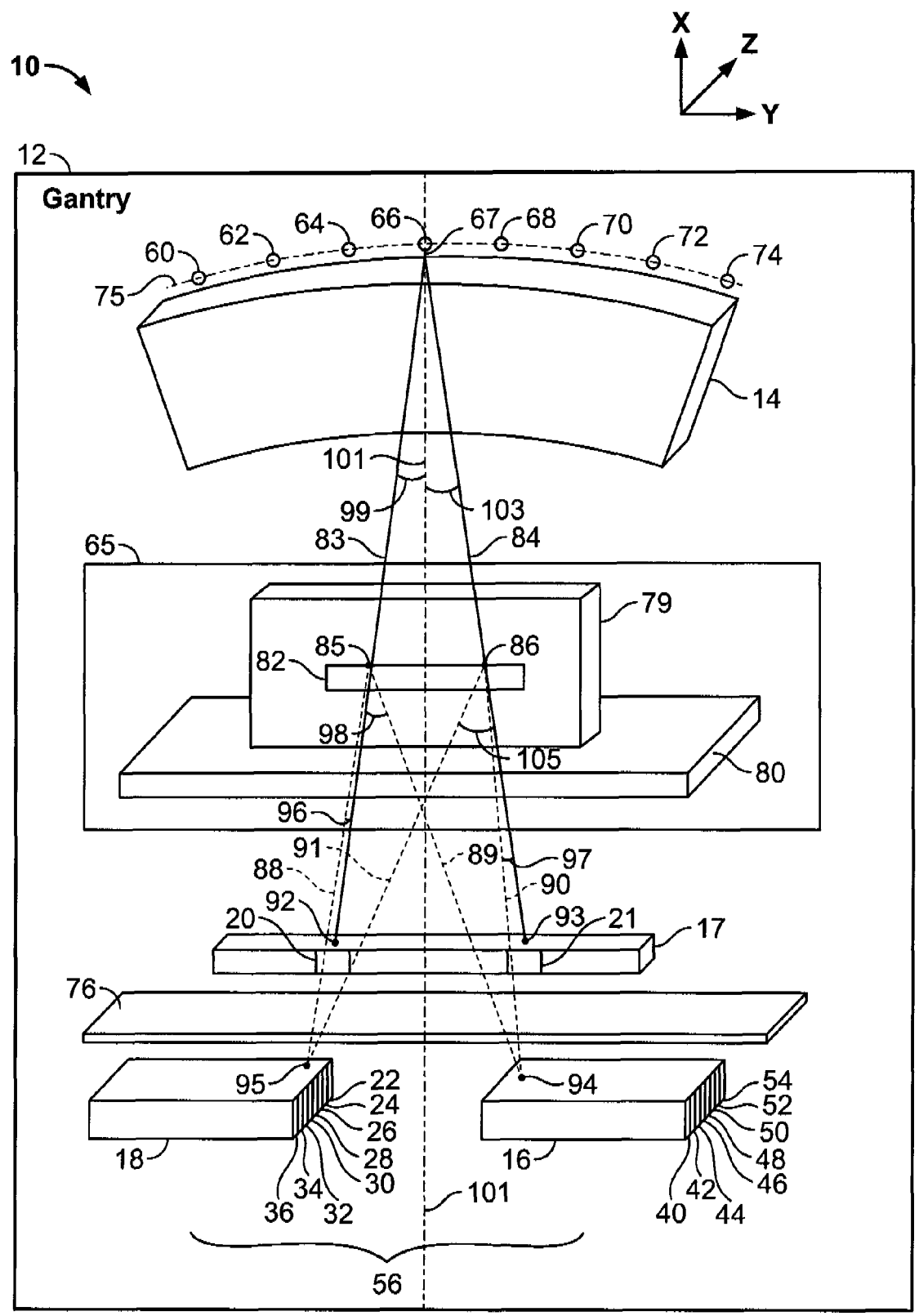
FIG. 1 is an isometric view of an embodiment of a system for identifying a substance.

FIG. 1 is an isometric view of an embodiment of a system 10 for identifying a substance. System 10 includes a gantry 12. Gantry 12 includes a primary collimator 14, a scatter detector 16, a transmission detector 17, a scatter detector 18, and a secondary collimator 76. Each scatter detector 16 and 18 is a segmented semiconductor detector.

Transmission detector 17 includes a plurality of detector cells or detector elements, such as detector elements 20 and 21. Scatter detector 18 includes a plurality of detector elements 22, 24, 26, 28, 30, 32, 34, and 36 for detecting coherent scatter. Scatter detector 16 includes a plurality of detector cells or detector elements 40, 42, 44, 46, 48, 50, 52, and 54 for detecting coherent scatter. Each of scatter detectors 16 and 18 include any number, such as, ranging from and including 5 to 1200, of detector elements. For example, scatter detector 18 includes a number, such as ranging from and including 5 to 40, of detector elements in a z-direction parallel to a z-axis, and a number, such as ranging from and including 1 to 30 detector elements in a y-direction parallel to a y-axis. An x-axis, the y-axis, and the z-axis are located within an xyz co-ordinate system. The x-axis is perpendicular to the y-axis and the z-axis, and the y-axis is perpendicular to the z-axis, and the x-axis is parallel to an x-direction. X-ray sources, of system 10, including x-ray sources 60, 62, 64, 66, 68, 70, 72, and 74, and transmission detector 17 form an inverse single-pass multi-focus imaging system. X-ray sources, of system 10, including x-ray sources 60, 62, 64, 66, 68, 70, 72, and 74, have an inverse fan-beam geometry that includes a symmetric location of the x-ray sources relative to the z-axis. A number of detector elements within scatter detector 16 is the same as a number of detector elements within scatter detector 18.

Scatter detector 16 is separate from scatter detector 18. For example, scatter detector 16 has a housing that is separate from a housing of scatter detector 18. As another example scatter detectors 16 and 18 are separated from each other by a gap. As yet another example, a shortest distance 56 between a center of scatter detector 16 and a center of scatter detector 18 ranges from and including 40 millimeters (mm) to 200 mm. Each of scatter detector 16, scatter detector 18, and transmission detector 17 are located in the same yz plane. The yz plane is formed by the y-axis and the z-axis. Each of scatter detector 16 and scatter detector 18 is separate from transmission detector 17 by a shortest distance ranging from and including 30 mm to 60 mm in the z-direction.

Gantry 12 further includes a plurality of x-ray sources 60, 62, 64, 66, 68, 70, 72, and 74. X-ray sources 60, 62, 64, 66, 68, 70, 72, and 74 are located parallel to and coincident with an arc 75. It is noted that in an alternative embodiment, system 10 includes a higher number, such as 10 or 20, or alternatively a lower number, such as 4 or 6, of x-ray sources than that shown in FIG. 1. A center of transmission detector 17 is located at a center of circle having arc 75. Each x-ray source 60, 62, 64, 66, 68, 70, 72, and 74 is an x-ray source that includes a cathode and an anode. Alternatively, each x-ray source 60, 62, 64, 66, 68, 70, 72, and 74 is an x-ray source that includes a cathode and all x-ray sources 60, 62, 64, 66, 68, 70, 72, and 74 share a common anode.

A container 79 is placed on a support 80 between x-ray sources 60, 62, 64, 66, 68, 70, 72, and 74 and scatter detectors 16 and 18. Container 79 and support 80 are located within an opening 65 of gantry 12. Examples of container 79 include a bag, a box, and an air cargo container 79. Examples of each x-ray source 60, 62, 64, 66, 68, 70, 72, and 74 include a polychromatic x-ray source. Container 79 includes a substance 82. Examples of substance 82 include an organic explosive, an amorphous substance having a crystallinity of less than twenty five percent, a quasi-amorphous substance having a crystallinity at least equal to twenty-five percent and less than fifty percent, and a partially crystalline substance having a crystallinity at least equal to fifty percent and less than one-hundred percent. Examples of the amorphous, quasi-amorphous, and partially crystalline substances include a gel explosive, a slurry explosive, an explosive including ammonium nitrate, and a special nuclear material. Examples of the special nuclear material include plutonium and uranium. Examples of support 80 include a table and a conveyor belt. An example of each scatter detector 16 and 18 includes a segmented detector fabricated from Germanium.

X-ray source 66 emits an x-ray beam 67 in an energy range, which is dependent on a voltage applied by a power source to x-ray source 66. Primary collimator 14 generates two primary beams 83 and 84, such as pencil beams, upon collimating x-ray beam 67 from x-ray source 66. In an alternative embodiment, primary collimator 14 collimates x-ray beam 67 received from x-ray source 66 to generates a plurality, such as three or fourth, primary beams. A number of primary beams generated by primary collimator 14 is equal to or alternatively greater than a number of scatter detectors on one side of transmission detector 17 and on one side of the y-axis. Primary beams 83 and 84 pass through a plurality of points 85 and 86 on substance 82 within container 79 arranged on support 80 to generate scattered radiation 88, 89, 90, and 91. For example, primary beam 83 passes through point 85 to generate scattered radiation 88 and 89. As another example, primary beam 84 passes through point 86 to generate scattered radiation 90 and 91.

Secondary collimator 76 is located between support 80 and a set of scatter detectors 16 and 18. Secondary collimator 76 includes a number of collimator elements, such as sheets, slits, or laminations, to ensure that scattered radiation arriving at scatter detectors 16 and 18 have constant scatter angles with respect to primary beams 83 and 84 and that a position of scatter detectors 16 and 18 permits a depth in container 79 at which the scattered radiation originated to be determined. For example, the collimator elements of secondary collimator 76 are arranged parallel to a direction of scattered radiation 88 and of scattered radiation 90 to absorb scattered radiation that is not parallel to the direction of the scattered radiation 88 and of scattered radiation 90.

The number of collimator elements in secondary collimator 76 provided is equal to or alternatively greater than a number of detector elements of any one of scatter detectors 16 and 18 and the collimator elements are arranged such that scattered radiation between neighboring collimator elements is incident on one of the detector elements. The collimator elements of scatter detectors 16 and 18 are made of a radiation-absorbing material, such as, steel, copper, silver, or tungsten.

Underneath support 80, there is arranged transmission detector 17, which measures an intensity of primary beam 83 at a point 92 on transmission detector 17 and an intensity of primary beam 84 at a point 93 on transmission detector 17. Moreover, underneath support 80, there are arranged scatter detectors 16 and 18 that measure photon energies of scattered radiation received by scatter detectors 16 and 18. Each of scatter detectors 16 and 18 measures the x-ray photons within scattered radiation received by scatter detectors 16 and 18 in an energy-sensitive manner by outputting a plurality of electrical output signals linearly dependent on a plurality of energies of the x-ray photons detected from within the scattered radiation. Scatter detector 16 measures scattered radiation 90 received at a point 94 on scatter detector 16 and scatter detector 18 measures scattered radiation 88 received at a point 95 on scatter detector 18. An example of a shortest distance between points 85 and 95 includes a distance ranging from and including 900 mm to 1100 mm. An example of a distance between points 95 and 92 includes a distance ranging from and including 25 mm to 80 mm.

Scatter detectors 16 and 18 detect scattered radiation to generate a plurality of electrical output signals. Scatter detector 16 detects scattered radiation 90 generated upon intersection of primary beam 84 with point 86. Moreover, scatter detector 16 detects scattered radiation 89 generated upon intersection of primary beam 83 with point 85. Scatter detector 18 detects scattered radiation 88 generated upon intersection of primary beam 83 with point 85. Moreover, scatter detector 18 detects scattered radiation 91 generated upon intersection of primary beam 84 with point 86. A scatter angle 96 formed between primary beam 83 and scattered radiation 88 is equal to a scatter angle 97 formed between primary beam 84 and scattered radiation 90. An example of each of scatter angles 96 and 97 includes an angle ranging from and including 0.025 radians to 0.045 radians. An example of a scatter angle 98 formed between primary beam 83 and scattered radiation 89 ranges from and including 0.05 radians to 0.09 radians. Moreover, an example of a scatter angle 105 formed between primary beam 84 and scattered radiation 91 ranges from and including 0.05 radians to 0.09 radians. Scatter angle 98 is at least twice of each scatter angle 96 and 97 and scatter angle 105 is at least twice of each scatter angle 96 and 97. An angle 99 formed by primary beam 83 with respect to a center 101 between scatter detectors 16 and 18 is equal to an angle 103 formed by primary beam 84 with respect to center 101. In another alternative embodiment, system 10 includes additional scatter detectors other than scatter detectors 16 and 18. The additional scatter detectors are placed on a side of transmission detector 17 that is the same as a side of placement of scatter detectors 16 and 18. Moreover, the additional scatter detectors are the same as scatter detectors 16 and 18. For example, any one of the additional scatter detectors have the same number of detector elements as that of any of scatter detectors 16 and 18. In an alternative embodiment, system 10 includes a beam selector 111 (shown in FIG. 2) that is activated to attenuate, such as filter, an x-ray beam, such as primary beam 84. In an alternative embodiment, system 10 includes beam selector 111 that is not activated or deactivated and so does not attenuate primary beams 83 and 84.

Figure 2:
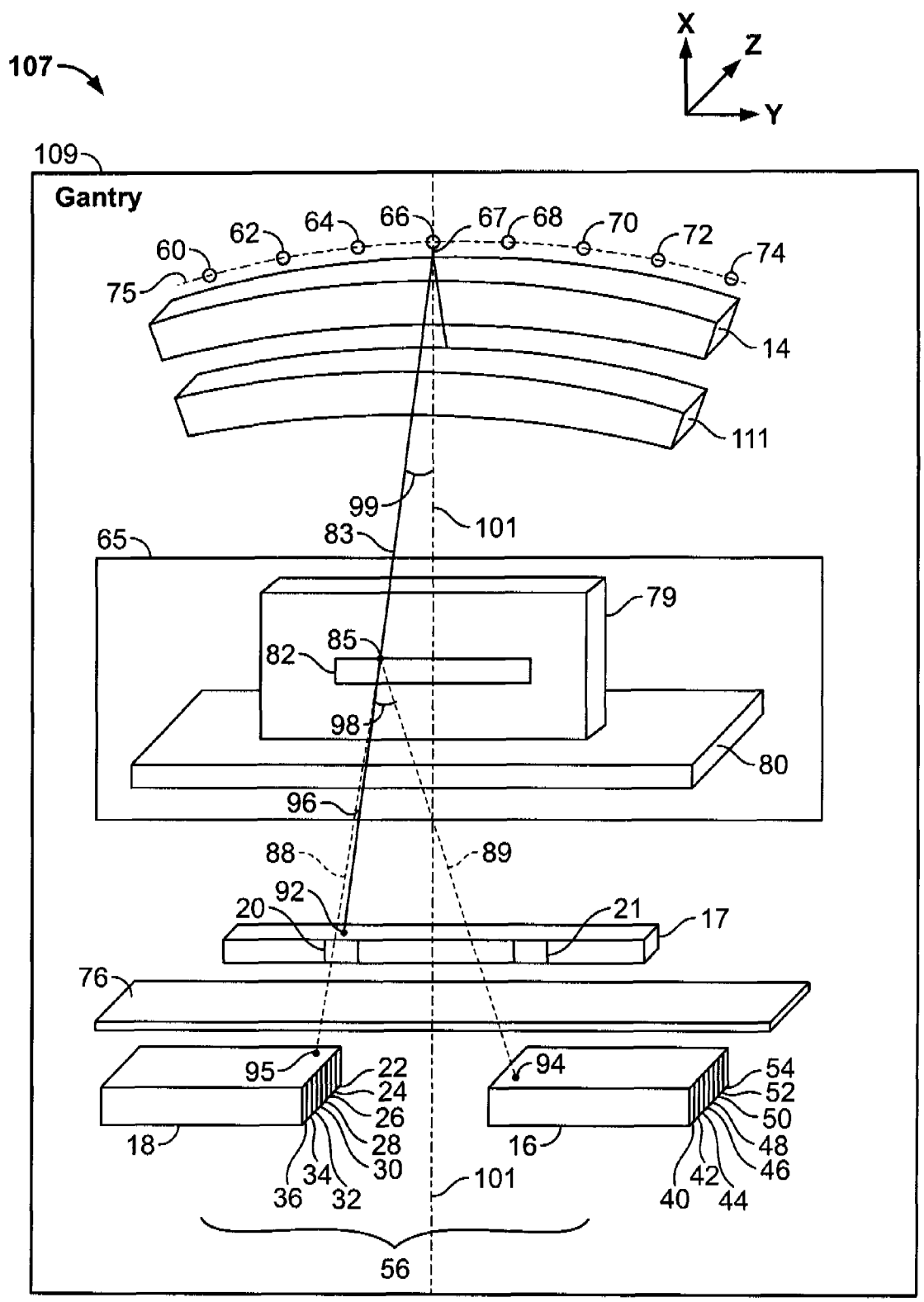
FIG. 2 is a block diagram of another embodiment of the system for identifying a substance.

FIG. 2 is a block diagram of an embodiment of a system 107 for identifying a substance. System 107 is an example of system 10 and includes a gantry 109, which includes beam selector 111. Beam selector 111 may be controlled by pneumatic, electrowetting, or alternatively electromechanical forces. An example of the pneumatic forces includes forces provided by a piston. An example of the electromechanical forces includes forces provided by a relay. Gantry 109 is an example of gantry 12. System 107 operates in a similar manner to that of system 10 except that beam selector 111 is activated to attenuate, such as filter, primary beam 84 from being received by container 79. When primary beam 84 is attenuated, primary beam 84 is not received by container 79, scattered radiation 90 and 91 are not output from container 79, scatter detector 16 does not detect scattered radiation 90, and scatter detector 18 does not detect scattered radiation 91. Beam selector 111 is not activated to attenuate primary beam 83. Scatter detector 18 detects scattered radiation 88 and scatter detector 16 detects scattered radiation 89 when primary beam 83 is not attenuated.

Figure 3:
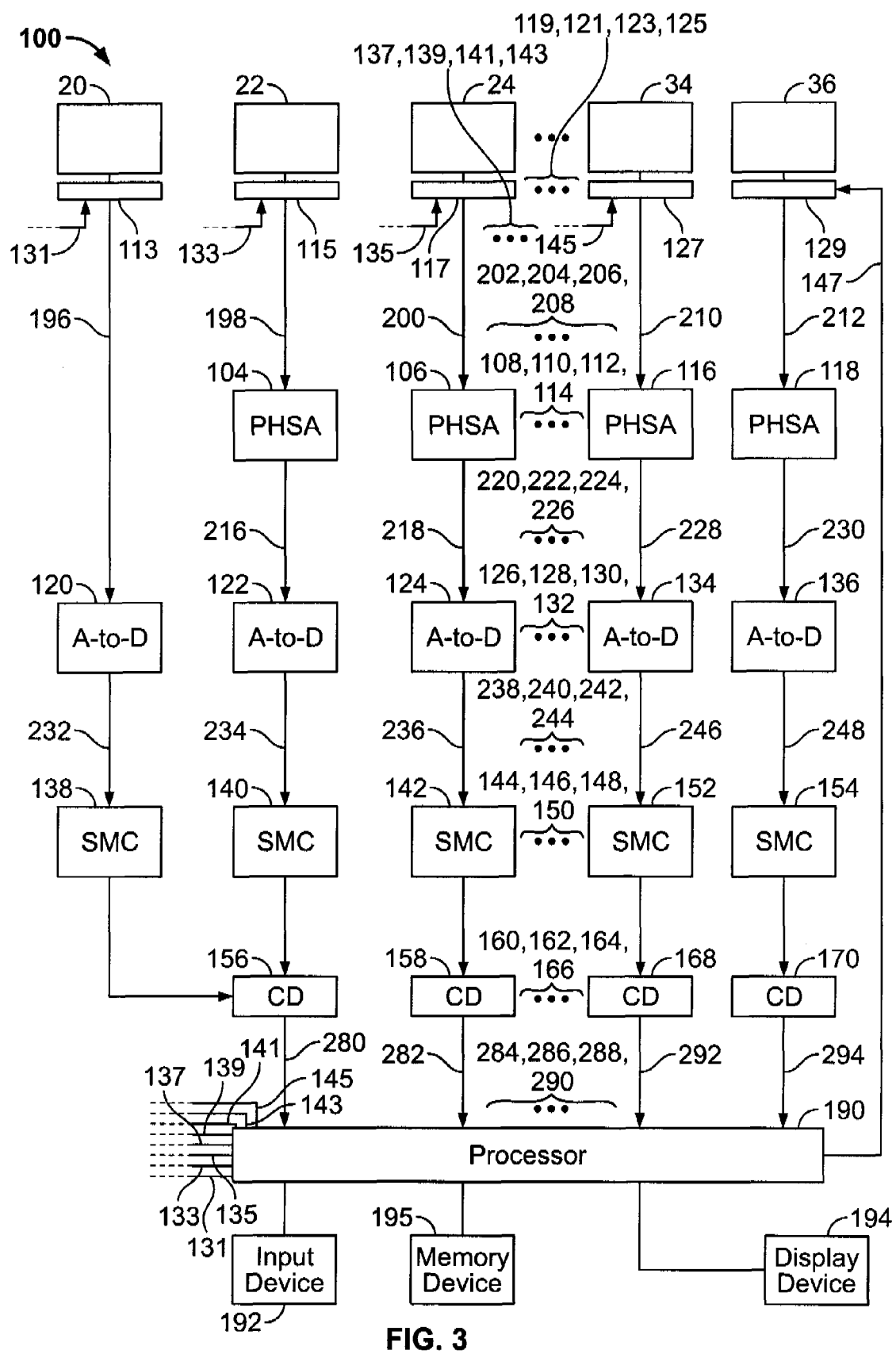
FIG. 3 is diagram of an embodiment of a system for identifying a substance.

FIG. 3 is diagram of an embodiment of a system 100 for identifying a substance. System 100 includes detector element 20 of transmission detector 17, scatter detector elements 22, 24, 26, 28, 30, 32, 34, and 36, a plurality of switches 113, 115, 117, 119, 121, 123, 125, 127, and 129, a plurality of pulse-height shaper amplifiers (PHSA) 104, 106, 108, 110, 112, 114, 116, and 118, a plurality of analog-to-digital (A-to-D) converters 120, 122, 124, 126, 128, 130, 132, 134, and 136, a plurality of spectrum memory circuits (SMCs) 138, 140, 142, 144, 146, 148, 150, 152, and 154 allowing pulse height spectra to be acquired, a plurality of correction devices (CDs) 156, 158, 160, 162, 164, 166, 168, and 170, a processor 190, an input device 192, a display device 194, and a memory device 195.

Processor 190 controls or activates beam selector 111 to attenuate an x-ray beam, such as primary beam 84. Processor 190 controls respective switches 113, 115, 117, 119, 121, 123, 125, 127, and 129 via a plurality of respective control lines 131, 133, 135, 137, 139, 141, 143, 145, and 147. For example, processor 190 closes switch 113 by sending a close control signal via control line 131. As another example, processor 190 closes switch 115 by sending a close control signal via control line 133. As yet another example, processor 190 opens switch 115 by sending an open control signal via control line 133. As used herein, the term processor is not limited to just those integrated circuits referred to in the art as a processor, but broadly refers to a computer, a microcontroller, a microcomputer, a programmable logic controller, an application specific integrated circuit, and any other programmable circuit. The computer may include a device, such as, a floppy disk drive or CD-ROM drive, for reading data including the methods for developing a primary collimator from a computer-readable medium, such as a floppy disk, a compact disc-read only memory (CD-ROM), a magneto-optical disk (MOD), or a digital versatile disc (DVD). In another embodiment, processor 190 executes instructions stored in firmware. Examples of display device 194 include a liquid crystal display (LCD) and a cathode ray tube (CRT). Examples of input device 192 include a mouse and a keyboard. Examples of memory device 195 include a random access memory (RAM) and a read-only memory (ROM). An example of each of correction devices 156, 158, 160, 162, 164, 166, 168, and 170 include a divider circuit. Each of spectrum memory circuits 138, 140, 142, 144, 146, 148, 150, 152, and 154 include an adder and a memory device, such as a RAM or a ROM. Examples of each switch 113, 115, 117, 119, 121, 123, 125, 127, and 129 includes a transistor, such as a field effect transistor or a bipolar junction transistor.

Detector element 20 is coupled to analog-to-digital converter 120 when processor 190 closes switch 113, and detector elements 22, 24, 26, 28, 30, 32, 34, and 36 are coupled to pulse-height shaper amplifiers 104, 106, 108, 110, 112, 114, 116, and 118, respectively when processor 190 closes respective switches 115, 117, 119, 121, 123, 125, 127, and 129. For example, when processor 190 closes switch 115, detector element 22 is coupled to pulse-height shaper amplifier 104. As another example, when processor 190 closes switch 117, detector element 24 is coupled to pulse-height shaper amplifier 106. On the other hand, detector element 20 is de-coupled from analog-to-digital converter 120, and detector elements 22, 24, 26, 28, 30, 32, 34, and 36 are de-coupled from pulse-height shaper amplifiers 104, 106, 108, 110, 112, 114, 116, and 118, respectively when processor 190 opens respective switches 113, 115, 117, 119, 121, 123, 125, 127, and 129. For example, when processor 190 opens switch 113, detector element 20 is de-coupled from analog-to-digital converter 120. As another example, when processor 190 opens switch 115, detector element 22 is de-coupled from pulse-height shaper amplifier 104.

Detector element 20 generates an electrical output signal 196 by detecting primary beam 83 and detector elements 22, 24, 26, 28, 30, 32, 34, and 36 generate a plurality of electrical output signals 198, 200, 202, 204, 206, 208, 210, and 212 by detecting scattered radiation when beam selector 111 attenuates primary beam 84 and does not attenuate primary beam 83. For example, detector element 22 generates electrical output signal 198 for each scattered x-ray photon incident on detector element 22 when beam selector 111 attenuates primary beam 84 and does not attenuate primary beam 83.

When processor 190 closes a switch, a pulse-height shaper amplifier amplifies an electrical output signal received from a detector element. For example, when processor 190 closes switches 115 and 117, pulse-height shaper amplifier 104 amplifies electrical output signal 198 and pulse-height shaper amplifier 106 amplifies electrical output signal 200. On the other hand, when processor 190 opens a switch, a pulse-height shaper amplifier does not receive an electrical output signal from a detector element. For example, when processor 190 opens switches 115 and 117, pulse-height shaper amplifier 104 does not receive electrical output signal 198 and pulse-height shaper amplifier 106 does not receive electrical output signal 200. Pulse-height shaper amplifiers 104, 106, 108, 110, 112, 114, 116, and 118 have a gain factor determined by processor 190.

An amplitude of an electrical output signal output from a detector element is proportional to an energy of an x-ray quantum that is detected by the detector element to generate the electrical output signal. For example, an amplitude of electrical output signal 196 is proportional to an energy of an x-ray quantum in primary beam 83 detected by detector element 20. As another example, an amplitude of electrical output signal 198 is proportional to an energy of an x-ray quantum within scattered radiation that is detected by detector element 22.

A pulse-height shaper amplifier generates an amplified output signal by amplifying an electrical output signal generated from a detector element. For example, pulse-height shaper amplifier 104 generates an amplified output signal 216 by amplifying electrical output signal 198 and pulse-height shaper amplifier 106 generates an amplified output signal 218 by amplifying electrical output signal 200. Similarly, a plurality of amplified output signals 220, 222, 224, 226, 228, and 230 are generated. An analog-to-digital converter converts an output signal from an analog form to a digital form to generate a digital output signal. For example, analog-to-digital converter 120 converts electrical output signal 196 from an analog form to a digital format to generate a digital output signal 232 and analog-to-digital converter 122 converts amplified output signal 216 from an analog form to a digital format to generate a digital output signal 234. Similarly, a plurality of digital output signals 236, 238, 240, 242, 244, 246, and 248 are generated by analog-to-digital converters 124, 126, 128, 130, 132, 134, and 136, respectively. A digital value of a digital output signal generated by an analog-to-digital converter represents an amplitude of energy of a pulse of an amplified output signal. Each pulse is generated by an x-ray quantum, such as an x-ray photon. For example, a digital value of digital output signal 234 output by analog-to-digital converter 122 is a value of an amplitude of a pulse of amplified output signal 216.

An adder of a spectrum memory circuit adds a number of pulses in a digital output signal. For example, when analog-to-digital converter 122 converts a pulse of amplified output signal 216 into digital output signal 234 to determine an amplitude of the pulse of amplified output signal 216, an adder within spectrum memory circuit 140 increments, by one, a value within a memory device of spectrum memory circuit 140. Accordingly, at an end of an x-ray examination of substance 82, a memory device within a spectrum memory circuit stores a number of x-ray quanta detected by a detector element. For example, a memory device within spectrum memory circuit 142 stores a number of x-ray photons detected by detector element 24 and each of the x-ray photons has an amplitude of energy or alternatively an amplitude of intensity that is determined by analog-to-digital converter 124.

A correction device receives a number of x-ray quanta that have a range of energies and are stored within a memory device of one of spectrum memory circuits 140, 142, 144, 146, 148, 150, 152, and 154, and divides the number by a number of x-ray quanta having the range of energies received from a memory device of spectrum memory circuit 138. For example, correction device 156 receives a number of x-ray photons having a range of energies from a memory device of spectrum memory circuit 140, and divides the number by a number of x-ray photons having the range received from a memory device of spectrum memory circuit 138. Each correction device outputs a correction output signal that represents a range of energies within x-ray quanta received by a detector element. For example, correction device 156 outputs a correction output signal 280 representing an energy spectrum or alternatively an intensity spectrum within x-ray quanta detected by detector element 22. As another example, correction device 158 outputs correction output signal 282 representing an energy spectrum within x-ray quanta detector element 24. Similarly, a plurality of correction output signals 284, 286, 288, 290, 292, and 294 are generated by correction devices 160, 162, 164, 166, 168, and 170, respectively. Processor 190 does not receive correction output signals 280, 282, 284, 286, 288, 290, 292, and 294 when processor 190 opens switches 113, 115, 117, 119, 121, 123, 125, 127, and 129. On the other hand, processor 190 receives correction output signals 280, 282, 284, 286, 288, 290, 292, and 294 when processor 190 closes switches 113, 115, 117, 119, 121, 123, 125, 127, and 129.

It is noted that a number of pulse-height shaper amplifiers 104, 106, 108, 110, 112, 114, 116, and 118 changes with a number of detector elements 22, 24, 26, 28, 30, 32, 34, and 36. For example, five pulse-height shaper amplifiers are used for amplifying signals received from five scatter detector elements. As another example, four pulse-height shaper amplifiers are used for amplifying signals received from four scatter detector elements. Similarly, a number of analog-to-digital converters 120, 122, 124, 126, 128, 130, 132, 134, and 136 changes with a number of detector elements 20, 22, 24, 26, 28, 30, 32, 34, and 36 and a number of spectrum memory circuits 138, 140, 142, 144, 146, 148, 150, 152, and 154 changes with the number of detector elements 20, 22, 24, 26, 28, 30, 32, 34, and 36.

Figure 4:
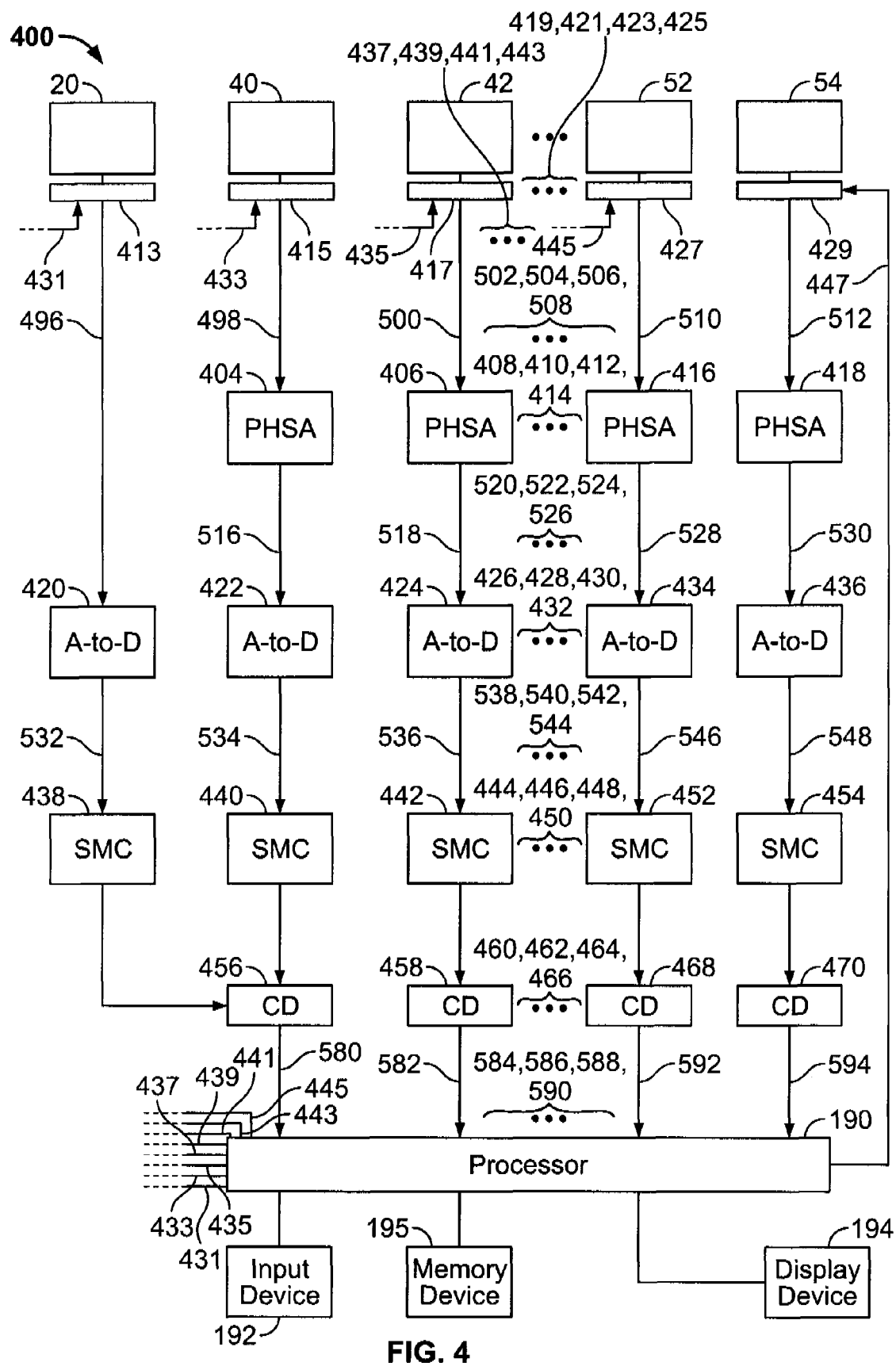
FIG. 4 is a diagram of an embodiment of a system for identifying a substance.

FIG. 4 is a diagram of an embodiment of a system 400 for identifying a substance. System 400 includes detector element 20 of transmission detector 17, scatter detector elements 40, 42, 44, 46, 48, 50, 52, and 54, a plurality of switches 413, 415, 417, 419, 421, 423, 425, 427, and 429, a plurality of pulse-height shaper amplifiers (PHSA) 404, 406, 408, 410, 412, 414, 416, and 418, a plurality of analog-to-digital (A-to-D) converters 420, 422, 424, 426, 428, 430, 432, 434, and 436, a plurality of spectrum memory circuits (SMCs) 438, 440, 442, 444, 446, 448, 450, 452, and 454 allowing pulse height spectra to be acquired, a plurality of correction devices (CDs) 456, 458, 460, 462, 464, 466, 468, and 470, processor 190, input device 192, display device 194, and memory device 195. An example of each of correction devices 456, 458, 460, 462, 464, 466, 468, and 470 include a divider circuit. Each of spectrum memory circuits 438, 440, 442, 444, 446, 448, 450, 452, and 454 include an adder and a memory device, such as a RAM or a ROM. Examples of each switch 413, 415, 417, 419, 421, 423, 425, 427, and 429 includes a transistor, such as a field effect transistor or a bipolar junction transistor. Processor 190 controls respective switches 413, 415, 417, 419, 421, 423, 425, 427, and 429 via a plurality of respective control lines 431, 433, 435, 437, 439, 441, 443, 445, and 447. For example, processor 190 closes switch 413 by sending a close control signal via control line 431. As another example, processor 190 closes switch 415 by sending a close control signal via control line 433. As yet another example, processor 190 opens switch 415 by sending an open control signal via control line 433.

Detector element 20 generates an electrical output signal 496 by detecting primary beam 84 and scatter detector elements 40, 42, 44, 46, 48, 50, 52, and 54 generate a plurality of electrical output signals 498, 500, 502, 504, 506, 508, 510, and 512 by detecting scattered radiation when beam selector 111 attenuates primary beam 84 and does not attenuate primary beam 83. For example, transmission detector element 20 generates electrical output signal 496 for x-ray photons incident on transmission detector element 20 when beam selector 111 attenuates primary beam 84 and does not attenuate primary beam 83.

Detector element 20 is coupled to analog-to-digital converter 420 when processor 190 closes switch 413 and scatter detector elements 40, 42, 44, 46, 48, 50, 52, and 54 are coupled to pulse-height shaper amplifiers 404, 406, 408, 410, 412, 414, 416, and 418, respectively when processor 190 closes respective switches 415, 417, 419, 421, 423, 425, 427, and 429. For example, when processor 190 closes switch 415, detector element 40 is coupled to pulse-height shaper amplifier 404. As another example, when processor 190 closes switch 417, detector element 42 is coupled to pulse-height shaper amplifier 406. On the other hand, detector element 20 is de-coupled from analog-to-digital converter 420, and detector elements 40, 42, 44, 46, 48, 50, 52, and 54 are de-coupled from pulse-height shaper amplifiers 404, 406, 408, 410, 412, 414, 416, and 418, respectively when processor 190 opens respective switches 413, 415, 417, 419, 421, 423, 425, 427, and 429. For example, when processor 190 opens switch 413, detector element 20 is de-coupled from analog-to-digital converter 420. As another example, when processor 190 opens switch 415, detector element 40 is de-coupled from pulse-height shaper amplifier 404.

When processor 190 closes a switch, each pulse-height shaper amplifier amplifies an electrical output signal received from a detector element. For example, when processor 190 closes switch 415, pulse-height shaper amplifier 404 amplifies electrical output signal 498. On the other hand, when processor 190 opens a switch, a pulse-height shaper amplifier does not receive an electrical output signal from a detector element. For example, when processor 190 opens switches 415 and 417, pulse-height shaper amplifier 404 does not receive electrical output signal 498 and pulse-height shaper amplifier 406 does not receive electrical output signal 500. Pulse-height shaper amplifiers 404, 406, 408, 410, 412, 414, 416, and 418 have a gain factor determined by processor 190.

An amplitude of an electrical output signal output from a detector element is proportional to an energy of an x-ray quantum that is detected by the detector element to generate the electrical output signal. For example, an amplitude of electrical output signal 496 is proportional to an energy of an x-ray quantum in primary beam 83 detected by detector element 20. As another example, an amplitude of electrical output signal 498 is proportional to an energy of an x-ray quantum within scattered radiation that is detected by detector element 40.

A pulse-height shaper amplifier generates an amplified output signal by amplifying an electrical output signal generated from a detector element. For example, pulse-height shaper amplifier 404 generates an amplified output signal 516 by amplifying electrical output signal 498 and pulse-height shaper amplifier 406 generates an amplified output signal 518 by amplifying electrical output signal 500. Similarly, a plurality of amplified output signals 520, 522, 524, 526, 528, and 530 are generated. An analog-to-digital converter converts an output signal from an analog form to a digital form to generate a digital output signal. For example, analog-to-digital converter 420 converts electrical output signal 496 from an analog form to a digital format to generate a digital output signal 532 and analog-to-digital converter 422 converts amplified output signal 516 from an analog form to a digital format to generate a digital output signal 534. Similarly, a plurality of digital output signals 536, 538, 540, 542, 544, 546, and 548 are generated by analog-to-digital converters 424, 426, 428, 430, 432, 434, and 436, respectively. A digital value of a digital output signal generated by an analog-to-digital converter represents an amplitude of energy or alternatively an amplitude of intensity of a pulse of an amplified output signal. Each pulse is generated by an x-ray quantum, such as an x-ray photon. For example, a digital value of digital output signal 534 output by analog-to-digital converter 422 is a value of an amplitude of a pulse of amplified output signal 516.

An adder of a spectrum memory circuit adds a number of pulses in a digital output signal. For example, when analog-to-digital converter 422 converts a pulse of amplified output signal 516 into digital output signal 534 to determine an amplitude of the pulse of amplified output signal 516, an adder within spectrum memory circuit 440 increments, by one, a value within a memory device of spectrum memory circuit 440. Accordingly, at an end of an x-ray examination of substance 82, a memory device within a spectrum memory circuit stores a number of x-ray quanta detected by a detector element. For example, a memory device within spectrum memory circuit 442 stores a number of x-ray photons detected by detector element 42 and each of the x-ray photons has an amplitude of energy that is determined by analog-to-digital converter 424.

A correction device receives a number of x-ray quanta that have a range of energies and are stored within a memory device of one of spectrum memory circuits 440, 442, 444, 446, 448, 450, 452, and 454, and divides the number by a number of x-ray quanta having the range of energies received from a memory device of spectrum memory circuit 438. For example, correction device 456 receives a number of x-ray photons having a range of energies from a memory device of spectrum memory circuit 440, and divides the number by a number of x-ray photons having the range received from a memory device of spectrum memory circuit 438. Each correction device outputs a correction output signal that represents a range of energies within x-ray quanta received by a detector element. For example, correction device 456 outputs a correction output signal 580 representing an energy spectrum or alternatively an intensity spectrum within x-ray quanta detected by detector element 40. As another example, correction device 458 outputs correction output signal 582 representing an energy spectrum within x-ray quanta detected by detector element 42. Similarly, a plurality of correction output signals 584, 586, 588, 590, 592, and 594 are generated by correction devices 460, 462, 464, 466, 468, and 470, respectively. Processor 190 does not receive correction output signals 580, 582, 584, 586, 588, 590, 592, and 594 when processor 190 opens switches 413, 415, 417, 419, 421, 423, 425, 427, and 429. On the other hand, processor 190 receives correction output signals 580, 582, 584, 586, 588, 590, 592, and 594 when processor 190 closes switches 413, 415, 417, 419, 421, 423, 425, 427, and 429.

It is noted that a number of pulse-height shape amplifiers 404, 406, 408, 410, 412, 414, 416, and 418 changes with a number of detector elements 40, 42, 44, 46, 48, 50, 52, and 54. For example, five pulse-height shaper amplifiers are used for amplifying signals received from five scatter detector elements. As another example, four pulse-height shaper amplifiers are used for amplifying signals received from four scatter detector elements. Similarly, a number of analog-to-digital converters 420, 422, 424, 426, 428, 430, 432, 434, and 436 changes with a number of detector elements 20, 40, 42, 44, 46, 48, 50, 52, and 54, and a number of spectrum memory circuits 438, 440, 442, 444, 446, 448, 450, 452, and 454 changes with the number of detector elements 20, 40, 42, 44, 46, 48, 50, 52, and 54.

Processor 190 closes switches 113, 115, 117, 119, 121, 123, 125, 127, and 129 and opens switches 413, 415, 417, 419, 421, 423, 425, 427, and 429 to receive correction output signals 280, 282, 284, 286, 288, 290, 292, 294. When switches 113, 115, 117, 119, 121, 123, 125, 127, and 129 are closed and switches 413, 415, 417, 419, 421, 423, 425, 427, and 429 are open, processor 190 receives correction output signals 280, 282, 284, 286, 288, 290, 292, 294 to generate a momentum transfer m, measured in inverse nanometers ($nm^{-1}$), from an energy spectrum $r(E_A)$ of energy $E_A$ of x-ray quanta within scattered radiation, including scattered radiation 88, detected by scatter detector 18 (FIG. 1). Processor 190 generates the momentum transfer m by applying $$m=(E_A/hc)\sin(\theta_A/2) \tag{1}$$

where c is a speed of light, h is Planck's constant, $\theta_A$ represents constant scatter angles of x-ray quanta of scattered radiation, including scattered radiation 88, detected by scatter detector 18. An example of $\theta_A$ includes scatter angle 96. Processor 190 relates the energy $E_A$ to the momentum transfer m by equation (1). Mechanical dimensions of secondary collimator 76 define the scatter angle $\theta_A$. Secondary collimator 76 restricts scattered radiation that does not have the angle $\theta_A$. Processor 190 receives the scatter angle θA from a user, such as a human being, via input device 192.

Processor 190 closes switches 413, 415, 417, 419, 421, 423, 425, 427, and 429 and opens switches 113, 115, 117, 119, 121, 123, 125, 127, and 129 to receive correction output signals 580, 582, 584, 586, 588, 590, 592, and 594. When switches 413, 415, 417, 419, 421, 423, 425, 427, and 429 are closed and switches 113, 115, 117, 119, 121, 123, 125, 127, and 129 are open, processor 190 receives correction output signals 580, 582, 584, 586, 588, 590, 592, and 594 to generate the momentum transfer m from an energy spectrum $r(E_B)$ of energy $E_B$ of x-ray quanta within scattered radiation, including scattered radiation 89, detected by scatter detector 16 (FIG. 1). Processor 190 generates the momentum transfer m by applying $$m=(E_B/hc)\sin(\theta_B/2) \tag{2}$$

where $\theta_B$ represents constant scatter angles of x-ray quanta of scattered radiation, including scattered radiation 89, detected by scatter detector 16 (FIG. 1). An example of $\theta_B$ includes scatter angle 98. Processor 190 relates the energy $E_B$ to the momentum transfer m by equation (2). Processor 190 receives the scatter angle θB from the user via input device 192.

Figure 5:
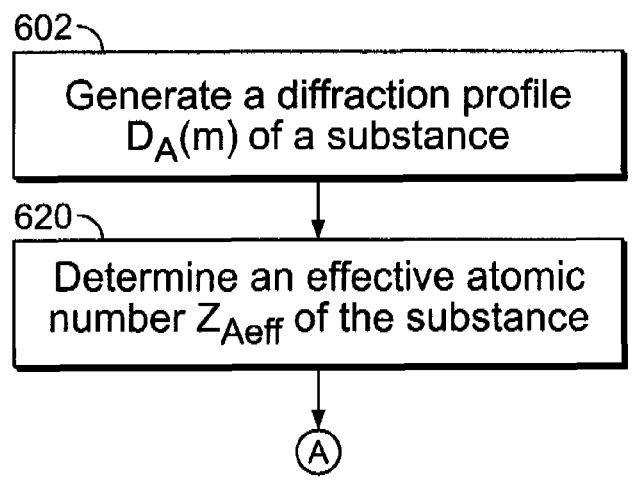
FIG. 5 is a flowchart of an embodiment of a method for identifying a substance.
Figure 6:
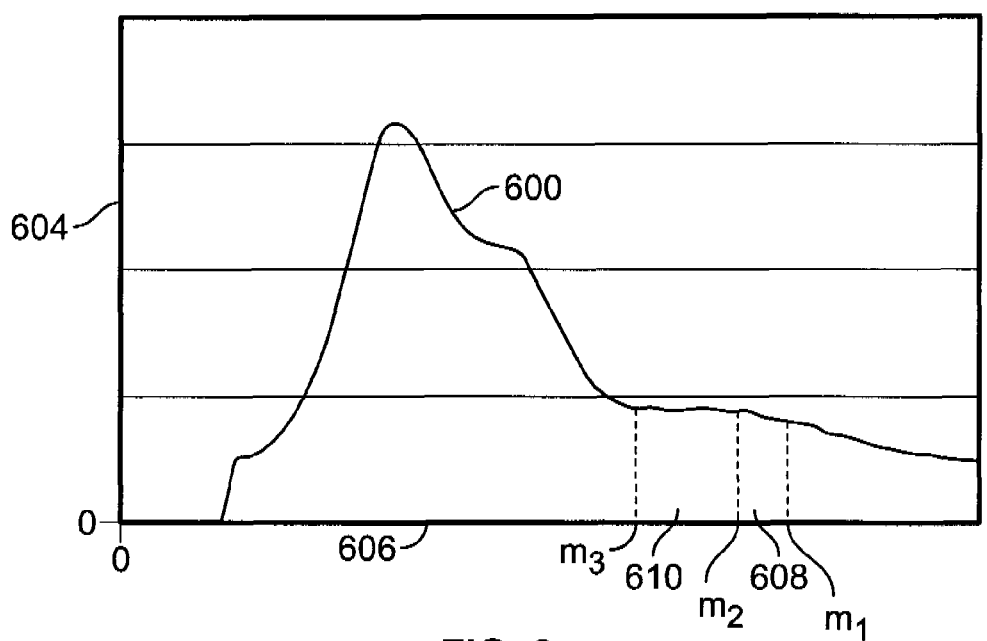
FIG. 6 shows an embodiment of a diffraction profile generated by a processor of the system of FIG. 3.

FIG. 5 is a flowchart of an embodiment of a method for identifying a substance and FIG. 6 shows a graph 600 or a diffraction profile $D_A(m)$ generated 602 by processor 190. Graph 600 is a histogram having a plurality of intensity values at a plurality of momentum transfer values, such as $m_1$, $m_2$, and $m_3$, of the momentum transfer m of equation (1). As an example, when an operating voltage of one of x-ray sources 60, 62, 64, 66, 68, 70, 72, and 74 is 160 kilovolts, processor 190 calculates, by applying equation (1), an energy value $E_{A1}$ of the energy $E_A$ to be 160 kilo electron volts (keV), calculates, by applying equation (1), an energy value $E_{A2}$ of the energy $E_A$ to be 140 keV, and calculates, by applying equation (1), an energy value $E_{A3}$ of the energy value $E_A$ to be photon energy 120 keV. In the example, the photon energy values $E_{A1}$, $E_{A2}$, and $E_{A3}$ correspond, through equation (1), to $m_1$ of four inverse nanometers of the momentum transfer m, $m_2$ of 3.5 inverse nanometers of the momentum transfer m, and to $m_3$ of three inverse nanometers of the momentum transfer m of equation (1), respectively. Graph 600 represents a histogram of a number of x-ray photons within scattered radiation, including scattered radiation 88, detected by scatter detector 18 versus the momentum transfer m of the x-ray photons when switches 113, 115, 117, 119, 121, 123, 125, 127, and 129 are closed, switches 413, 415, 417, 419, 421, 423, 425, 427, and 429 are open, and primary beam 84 is attenuated. A number of photons detected by scatter detector 18 is plotted along an ordinate 604 and the momentum transfer m of equation (1) is plotted along an abscissa 606. As an example, abscissa 606 extends from and including zero inverse nanometers to at most 10 inverse nanometers. An example of a total number of bins of numbers of x-ray photons plotted on ordinate 604 lies between 64 and 900. An example of a number of x-ray photons detected by scatter detector 18 per examination lies between 1000 and 80,000.

The diffraction profile $D_A(m)$ ranging from $m \geq 3$ $mm^{-1}$ is dominated by coherent scatter from free atoms of substance 82. In a tip region $TR_A$, extending from $m_1$ to $m_3$, of graph 600, an intensity of scattered radiation, including scattered radiation 88, detected by scatter detector 18 when switches 113, 115, 117, 119, 121, 123, 125, 127, and 129 are closed, switches 413, 415, 417, 419, 421, 423, 425, 427, and 429 are open, and primary beam 84 is attenuated is proportional to a product of density, such as a mean density, of substance 82 and a power, such as ranging between 2.5 and 3.5, of a mean atomic number of a plurality of materials within substance 82.

A number of x-ray photons that are scattered with momentum transfer values between $m_1$ and $m_2$ are represented within a band 608 under graph 600. Processor 190 determines a cumulative number of x-ray photons within band 608 by cumulatively summing a number of x-ray photons between momentum transfer values $m_1$ and $m_2$ on abscissa 606. A number of x-ray photons that are scattered with momentum transfer values between $m_2$ and $m_3$ are located within a band 610 under graph 600. Processor 190 determines a cumulative number of x-ray photons within band 610 by cumulatively summing a number of x-ray photons between momentum transfer values $m_2$ and $m_3$ on abscissa 606.

Figure 7:
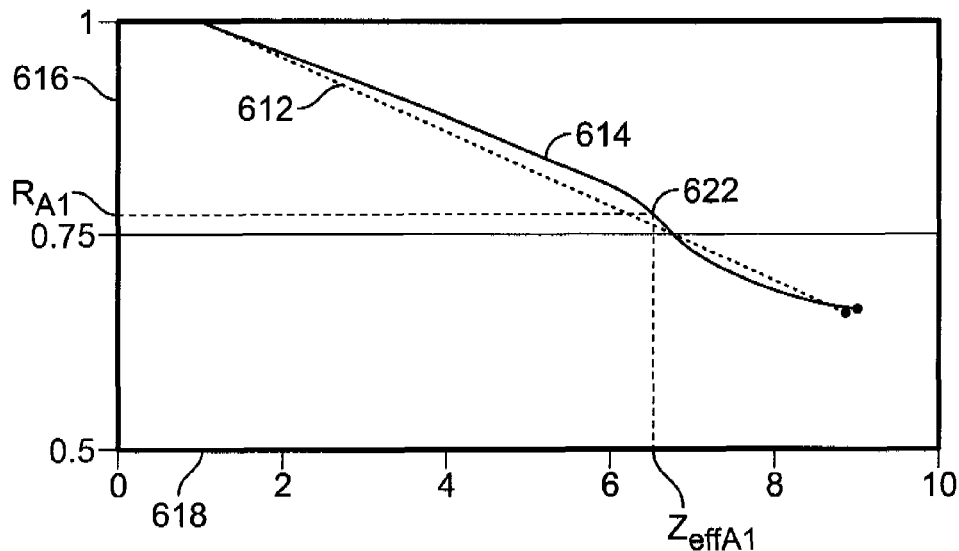
FIG. 7 shows an embodiment of a dotted line and a solid curve generated by the processor.

FIG. 7 shows a dotted line 612 and a solid curve 614 generated by processor 190. Solid curve 614 represents a theoretical relationship between a ratio of total free atom scatter cross-sections, referred to as total scatter cross-sections or cumulative scatter cross-sections, and an atomic number Z. As an example, processor 190 plots solid curve 614 from an example of the theoretical relationship mentioned in Hubbell, J. H., Veigele, W. J., Briggs, E. A., Brown, R. T., Cromer, D. T., Howerton, R. J., Atomic Form Factors, Incoherent Scattering Functions and Photon Scattering Cross-sections, Journal of Physics and Chemical Reference Data, Volume 4, page 471 (1975), Erratum: Atomic Form Factors, Incoherent Scattering Functions, and Photon Scattering Cross Sections, Journal of Physics and Chemical Reference Data, Volume 6, page 615 (1977). As another example, the theoretical relationship includes an atomic number value of oxygen as eight corresponding to a ratio of 0.68 of total scatter cross-sections calculated for oxygen. As yet another example, the theoretical relationship includes an atomic number value of carbon as six corresponding to a ratio of 0.73 of total scatter cross-sections calculated from carbon. Processor 190 generates dotted line 612 as a linear fit or linear regression to the theoretical relationship. A plurality of ratios of total scatter cross-sections are plotted along an ordinate 616 and a plurality of atomic numbers Z are measured along an abscissa 618.

Processor 190 calculates a ratio of cumulative numbers of x-ray photons within bands 608 and 610. For example, processor 190 determines that $R_{A1}$ is a ratio of a cumulative number of x-ray photons within band 608 to a cumulative number of x-ray photons within band 610. Processor 190 determines 620, by using solid curve 614, an effective atomic number $Z_{Aeff}$ corresponding to a ratio of a cumulative number of x-ray photons within band 608 and a cumulative number of x-ray photons within band 610. As an example, processor 190 perpendicularly extends a horizontal line from the ratio $R_{A1}$ to intersect solid curve 614 at an intersection point 622 and extends a line from intersection point 622 to perpendicularly intersect abscissa 618 at an effective atomic number value $Z_{Aeff1}$ of the effective atomic number $Z_{Aeff}$. Alternatively, processor 190 determines, by using dotted line 612, the effective atomic number $Z_{Aeff}$ corresponding to a ratio of a cumulative number of x-ray photons within band 608 and a cumulative number of x-ray photons within band 610. As an example, processor 190 perpendicularly extends a horizontal line from the ratio $R_{A1}$ to intersect dotted line 612 at an intersection point and extends a line from the intersection point to perpendicularly intersect abscissa 618 at an effective atomic number value $Z_{Aeff2}$.

Figure 8:
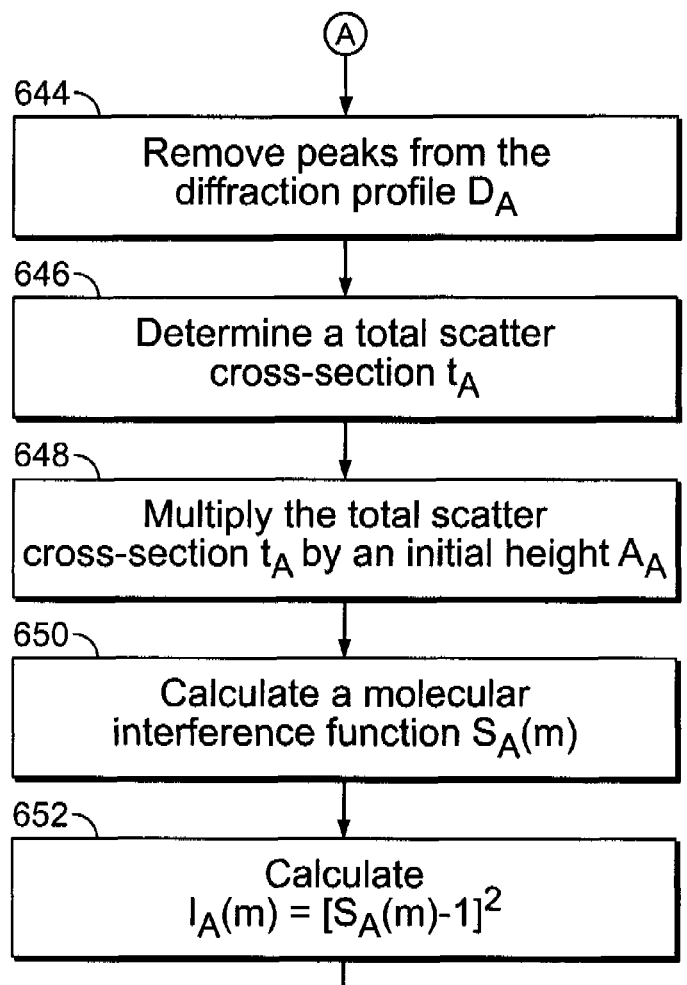
FIG. 8 is a continuation of the flowchart of FIG. 5.
Figure 9:
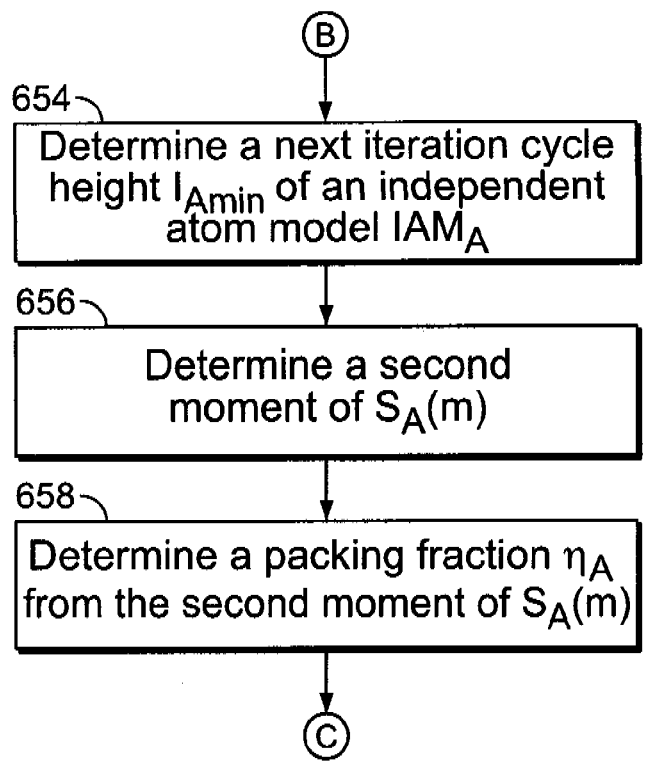
FIG. 9 is a continuation of the flowchart of FIG. 8.
Figure 10:
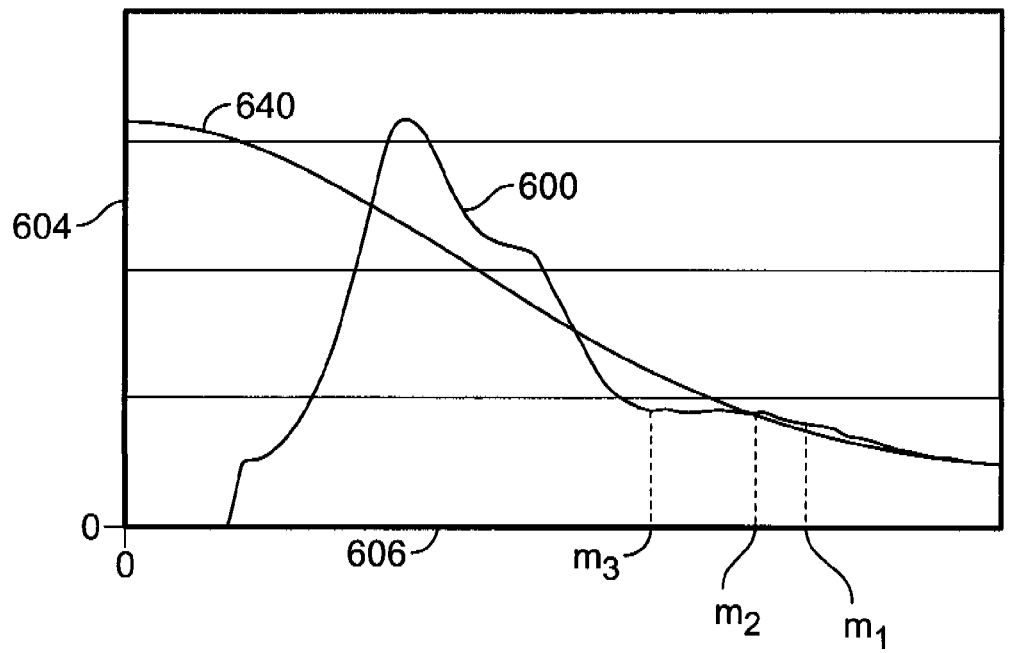
FIG. 10 shows an embodiment of an independent atom model curve generated by the processor.
Figure 11:
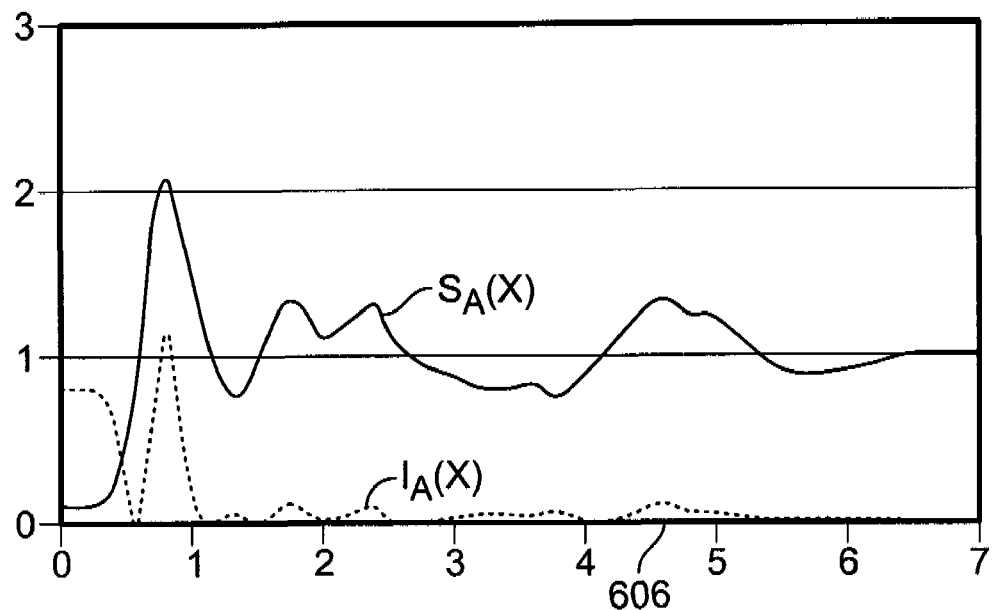
FIG. 11 shows a plurality of embodiments of a plurality of graphs generated by the processor.

FIGS. 8-9 are a flowchart of an embodiment of a method for identifying a substance, FIG. 10 shows an embodiment of an independent atom model ($IAM_A$) curve 640 generated by processor 190, and FIG. 11 shows a plurality of embodiments of a plurality of graphs $S_A(m)$ and $I_A(m)$ generated by processor 190.

The graph $S_A(m)$ represents a molecular interference function and the graph $I_A(m)$ represents an approximation function. Processor removes 644 a plurality of crystalline interference peaks from graph 600 by applying a peak removal algorithm. An example of the peak removal algorithm is provided in a software, such as an "OptiFit" computer software, described in Rabiej M, Determination of the Degree of Crystallinity of Semicrystalline Polymers by Means of the "OptiFit" Computer Software, POLIMERY 6, pages 423-427 (2002). In an alternative embodiment, processor 190 removes all crystalline interference peaks that represent a crystallinity of substance 82 and that are located within the diffraction profile $D_A(m)$ by applying the peak removal algorithm. For example, in case of quasi-amorphous or alternatively partially crystalline substances, a plurality of crystalline interference peaks may be included within graph 600 and processor 190 removes the crystalline interference peaks by applying the peak removal algorithm. The peak removal algorithm is applied to generate a peak-removed graph, such as graph 600. The molecular interference function $S_A(m)$ is invalid if $S_A(m)$ does not tend to unity for values of m greater than values of m within the tip region $TR_A$. The molecular interference function $S_A(m)$ is valid if $S_A(m)$ tends to unity for values of m greater than values of m within the tip region $TR_A$.

Processor 190 determines 646 a total scatter cross-section $t_A$ of $IAM_A$ curve 640 from the effective atomic number $Z_{Aeff}$. For example, upon determining by processor 190 that the effective atomic number value $Z_{effA1}$ is a first rational number, such as 6.3, processor 190 generates a weighted average $W_A$ of a plurality of $IAM_A$ functions corresponding to neighboring atomic numbers six and seven. In the example, processor 190 generates the weighted average $W_A$, such as $\frac{1}{3}[IAM_A(6)]+\frac{2}{3}[IAM_A(7)]$, where $IAM_A(6)$ is a total scatter cross-section for carbon and $IAM_A(7)$ is a total scatter cross-section for nitrogen. An example of the $IAM_A$ functions corresponding to neighboring atomic numbers are available in Hubbell, J. H., Veigele, W. J., Briggs, E. A., Brown, R. T., Cromer, D. T., Howerton, R. J., Atomic Form Factors, Incoherent Scattering Functions and Photon Scattering Cross-sections, Journal of Physics and Chemical Reference Data, Volume 4, page 471 (1975), Erratum: Atomic Form Factors, Incoherent Scattering Functions, and Photon Scattering Cross Sections, Journal of Physics and Chemical Reference Data, Volume 6, page 615 (1977). The weighted average $W_A$ is an example of the total scatter cross-section $t_A$, determined in 646, of $IAM_A$ curve 640.

Alternatively, instead of generating the weighted average $W_A$, upon determining by processor 190 that the effective atomic number value $Z_{Aeff1}$ is the first rational number, processor 190 generates a closest total scatter cross-section of $IAM_A$ curve 640 corresponding to an atomic number value, which is an integer closest to the first rational number and plots, with respect to ordinate 604, the closest total scatter cross-section. In yet another alternative embodiment, instead of generating the weighted average $W_A$, upon determining by processor 190 that the effective atomic number value $Z_{Aeff1}$ is the first rational number, processor 190 generates a first universal total scatter cross-section of $IAM_A$ curve 640 by scaling the momentum transfer m of $IAM_A$ curve 640. As an example, abscissa 606 is scaled by multiplying the momentum transfer m of $IAM_A$ curve 640 with $0.02Z_{Aeff1}+0.12$ to generate the first universal total scatter cross-section of $IAM_A$ curve 640.

Processor 190 multiplies 648 the total scatter cross-section $t_A$, determined in 646, by an initial amplitude $A_A$ or an initial height to generate a first iteration cycle free atom curve $C_A$. For example, processor 190 multiplies each value of the total scatter cross-section $t_A$, determined in 646, with the initial height $A_A$ to generate the first iteration cycle free atom curve $C_A$. Processor 190 receives the initial height $A_A$ from the user via input device 192. Processor 190 calculates 650 the molecular interference function $S_A(m)$ by dividing a number of x-ray photons represented by graph 600 by the first iteration cycle free atom curve $C_A$. As an example, processor 190 generates a molecular interference value $S_{A1}(m)$ of the molecular interference function $S_A(m)$ by dividing a number of x-ray photons having the momentum transfer value $m_1$ that lies on graph 600 by a number of x-ray photons having the momentum transfer value $m_1$ that lies on the first iteration cycle free atom curve $C_A$. As another example, processor 190 generates a molecular interference value $S_{A2}(m)$ of the molecular interference function $S_A(m)$ by dividing a number of x-ray photons having the momentum transfer value $m_2$ that lies on graph 600 by a number of x-ray photons having the momentum transfer value $m_2$ that lies on first iteration cycle free atom curve $C_A$.

Processor 190 calculates 652 the approximation function $I_A(m)$ as $$I_A(m) = [s_A(m)-1]^2 \quad (3)$$

Processor 190 determines 654 a next iteration cycle amplitude $I_{Amin}$ or a next iteration cycle height of $IAM_A$ curve 640 by minimizing an integral of $I_A(m)$ represented as $$\int_0^{m_{max}} I_A(m)\,dm \quad (4)$$

where $m_{max}$ is the largest value of m on abscissa 606 of graph 600 and $IAM_A$ curve 640. For example, processor 190 determines the next iteration cycle height $I_{Amin}$ by selecting a minimum from a first and a second calculated value. Processor 190 determines the first calculated value by applying 648, 650, and 652, and equation (4) to the initial height $A_A$. Processor 190 determines the second calculated value by applying 648, 650, 652, and equation (4) to a changed height $B_A$ instead of the initial height $A_A$. For example, processor 190 multiplies the total scatter cross-section $t_A$, determined in 646, by the changed height $B_A$ to generate a second iteration cycle free atom curve $C_{SA}$, calculates the molecular interference function $S_A(m)$ by dividing a number of x-ray photons represented by graph 600 by the second iteration cycle free atom curve $C_{SA}$, calculates the approximation function $I_A(m)$ from equation (3), and generates the second calculated value by applying equation (4). Processor 190 generates the changed height $B_A$ by modifying, such as incrementing or decrementing, the initial height $A_A$. As another example, processor 190 determines the next iteration cycle height $I_{Amin}$ by selecting a minimum from a plurality, such as three, of calculated values, such as the first calculated value, the second calculated value, and a third calculated value. Processor 190 generates the third calculated value in a similar manner in which first and second calculated values are generated. For example, processor 190 generates the third calculated value after incrementing or alternatively decrementing the changed height $B_A$.

Processor 190 determines 656 a second moment of $I_A(m)$ by applying $$M2S_A = \frac{\int_0^\infty m^2 I_{Amin}(m)\,dm}{\int_0^\infty I_{Amin}(m)\,dm} \quad (5)$$

Processor 190 determines 658 a packing fraction $\eta_A$ of substance 82 as being linearly proportional, such as equal, to the second moment $M2S_A$. The packing fraction $\eta_A$ is linearly proportional to the second moment $M2S_A$ when substance 82 includes a plurality of identical hard spheres over a range of $\eta_A$ of amorphous materials relevant in explosive and/or contraband detection. An example of the linearly proportional relationship includes $$\eta_A = a(M2S_A) \quad (6)$$

where a is a coefficient received by processor 190 via input device 192 from the user, and a ranges from and including 0.1 to 0.2.

Figure 12:
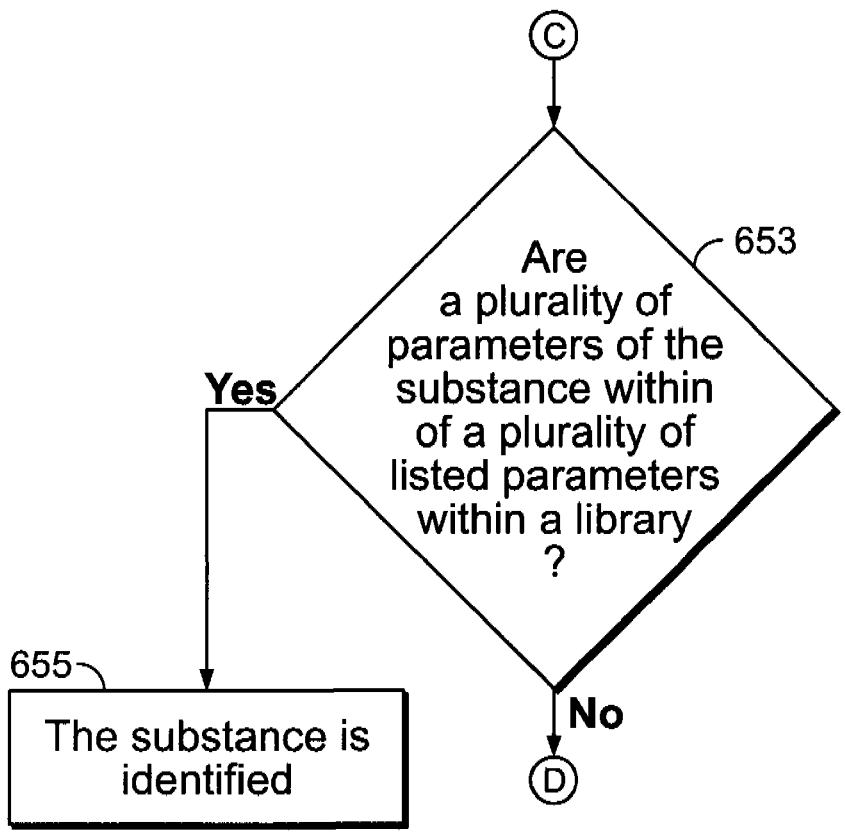
FIG. 12 is a continuation of the flowchart of FIG. 9.

FIG. 12 is a flowchart of an embodiment of a method for identifying a substance. Processor 190 determines 653 whether the diffraction profile $D_A(m)$, the effective atomic number $Z_{Aeff}$, and the packing fraction $\eta_A$ are within a threshold, such as ranging from and including zero to ten percent, of a plurality of sets of listed parameters within a library or a library file stored within memory device 195. An example of a first one of the sets of listed parameters within the library include a diffraction profile $D_{II}$ of a substance II, an effective atomic number $Z_{IIeff}$ of the substance II, and a packing fraction $\eta_{II}$ of the substance II, and an example of a second one of the sets of listed parameters include a diffraction profile $D_{III}$ of a substance III, an effective atomic number $Z_{IIIeff}$ of the substance III, and a packing fraction $\eta_{III}$ of the substance III. The library may include the listed parameters of a number of other substances, such as a substance IV and substance V.

The substances II, III, IV, and V having the listed parameters are known or identified substances, such as, Danubit, Semtex, heroin, ecstasy, and cocaine. The listed parameters are input into the library of memory device 195 by the user via input device 192. An example of the determination 653 made by processor 190 includes determining whether the diffraction profile $D_A(m)$ is within the threshold of the diffraction profile $D_{III}$, whether the effective atomic number $Z_{Aeff}$ is within the threshold of the effective atomic number $Z_{IIIeff}$, and the packing fraction $\eta_A$ is within the threshold of the packing fraction $\eta_{III}$. Another example of the determination 653 made by processor 190 includes determining whether the diffraction profile $D_A(m)$ is within the threshold of the diffraction profile $D_{II}$, whether the effective atomic number $Z_{Aeff}$ is within the threshold of the effective atomic number $Z_{IIeff}$, and the packing fraction $\eta_A$ is within the threshold of the packing fraction $\eta_{II}$. As an example, processor 190 determines whether the diffraction profile $D_A(m)$ is within the threshold of the diffraction profile $D_{II}$ by determining whether a number of x-ray photons, plotted on the diffraction profile $D_A(m)$, at the momentum transfer value $m_1$ is within the threshold of a number of x-ray photons, plotted on the diffraction profile $D_{II}$, at the momentum transfer value $m_1$. As another example, processor 190 determines whether the diffraction profile $D_A(m)$ is within the threshold of the diffraction profile $D_{II}$ by determining whether a number of x-ray photons, plotted on the diffraction profile $D_A(m)$, at the momentum transfer value $m_2$ is within the threshold of a number of x-ray photons, plotted on the diffraction profile $D_{II}$, at the momentum transfer value $m_2$. Upon determining that the diffraction profile $D_A(m)$, the effective atomic number $Z_{Aeff}$, and the packing fraction $\eta_A$ are within the threshold of the plurality of listed parameters within the library, processor 190 determines 655 that substance 82 is identified as having one of the sets of listed parameters that are within the threshold of the diffraction profile $D_A(m)$, the effective atomic number $Z_{Aeff}$, and the packing fraction $\eta_A$.

In an alternative embodiment, processor 190 determines whether at least one of the diffraction profile $D_A(m)$, the effective atomic number $Z_{Aeff}$, and the packing fraction $\eta_A$ is within the threshold of at least one of the listed parameters within one of the sets of the library. For example, processor 190 determines whether the diffraction profile $D_A(m)$ is within the threshold of the diffraction profile $D_{II}$. As another example, processor 190 determines whether the effective atomic number $Z_{Aeff}$ is within the threshold of the effective atomic number $Z_{IIeff}$. As yet another example, processor 190 determines whether the effective atomic number $Z_{Aeff}$ is within the threshold of the effective atomic number $Z_{IIeff}$ and whether the packing fraction $\eta_A$ is within the threshold of the packing fraction $\eta_{II}$. In the alternative embodiment, upon determining that at least one of the diffraction profile $D_A(m)$, the effective atomic number $Z_{Aeff}$, and the packing fraction $\eta_A$ is within the threshold of at least one of the listed parameters within one of the sets of the library, processor 190 determines that substance 82 is identified as having the one of the sets of listed parameters having the at least one of the listed parameters within the threshold of the at least one of the diffraction profile $D_A(m)$, the effective atomic number $Z_{Aeff}$, and the packing fraction $\eta_A$.

Figure 13:
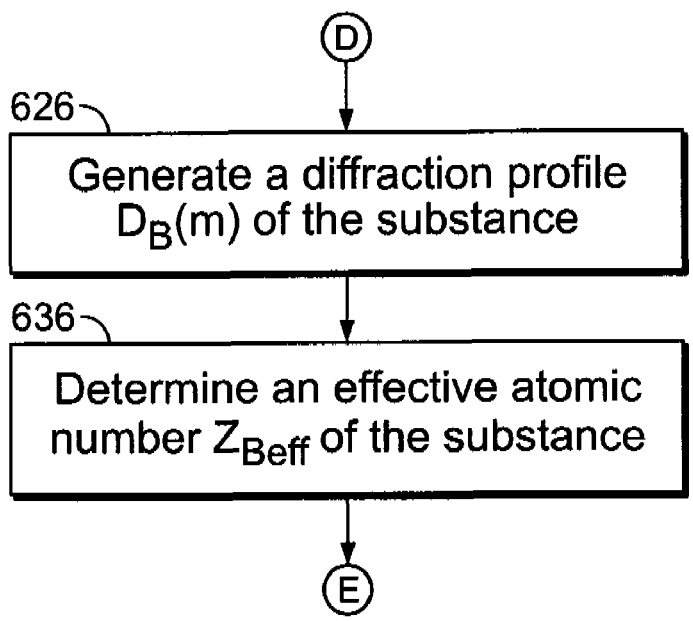
FIG. 13 is a continuation of the flowchart of FIG. 12.
Figure 14:
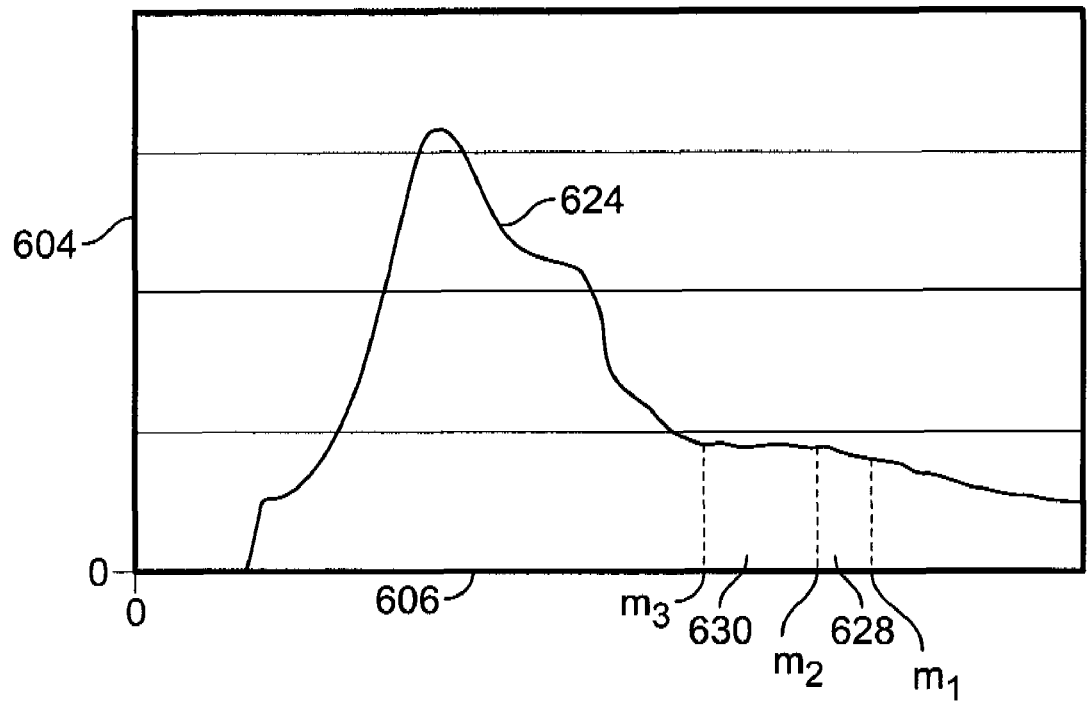
FIG. 14 shows another embodiment of a diffraction profile generated by the processor.

FIG. 13 is a flowchart of an embodiment of a method for identifying a substance and FIG. 14 shows a graph 624 or a diffraction profile $D_B(m)$ generated 626 by processor 190. The diffraction profile $D_B(m)$ is generated 626 by processor 190 upon determining that the diffraction profile $D_A(m)$, the effective atomic number $Z_{Aeff}$, and the packing fraction $\eta_A$ are not within the threshold of the plurality of listed parameters within the library. In an alternative embodiment, the diffraction profile $D_B(m)$ is generated by processor 190 upon determining that at least one of the diffraction profile $D_A(m)$, the effective atomic number $Z_{Aeff}$, and the packing fraction $\eta_A$ is not within the threshold of at least one of the listed parameters within one of the sets of the library.

Graph 624 is a histogram having a plurality of intensity values at a plurality of momentum transfer values, such as $m_1$, $m_2$, and $m_3$, of the momentum transfer m of equation (2). As an example, when an operating voltage of one of x-ray sources 60, 62, 64, 66, 68, 70, 72, and 74 is 160 kilovolts, processor 190 calculates, by applying equation (2), an energy value $E_{B1}$ of the energy $E_B$ to be 160 keV, calculates, by applying equation (2), an energy value $E_{B2}$ of the energy $E_B$ to be 140 keV, and calculates, by applying equation (2), an energy value $E_{B3}$ of the energy value $E_B$ to be photon energy 120 keV. In the example, the photon energy values $E_{B1}$, $E_{B2}$, and $E_{B3}$ correspond, through equation (2), to $m_1$ of four inverse nanometers of the momentum transfer m, $m_2$ of 3.5 inverse nanometers of the momentum transfer m, and to $m_3$ of three inverse nanometers of the momentum transfer m of equation (2), respectively. Graph 624 represents a histogram of a number of x-ray photons within scattered radiation, including scattered radiation 89, detected by scatter detector 16 versus the momentum transfer m of the x-ray photons when switches 413, 415, 417, 419, 421, 423, 425, 427, and 429 are closed, switches 113, 115, 117, 119, 121, 123, 125, 127, and 129 are open, and primary beam 84 is attenuated. A number of photons detected by scatter detector 16 is plotted along ordinate 604 and the momentum transfer m of equation (2) is plotted along abscissa 606. An example of a number of x-ray photons detected by scatter detector 16 per examination lies between 312 and 25,000.

The diffraction profile $D_B(m)$ ranging from $m \geq 3$ $nm^{-1}$ is dominated by coherent scatter from free atoms of substance 82. In a tip region $TR_B$, extending from $m_1$ to $m_3$, of graph 624, an intensity of scattered radiation, including scattered radiation 89, detected by scatter detector 16 when switches 413, 415, 417, 419, 421, 423, 425, 427, and 429 are closed, switches 113, 115, 117, 119, 121, 123, 125, 127, and 129 are open, and primary beam 84 is attenuated is proportional to a product of density, such as a mean density, of substance 82 and a power, such as ranging between 2.5 and 3.5, of a mean atomic number of a plurality of materials within substance 82.

A number of x-ray photons that are scattered with momentum transfer values between $m_1$ and $m_2$ are represented within a band 628 under graph 624. Processor 190 determines a cumulative number of x-ray photons within band 628 by cumulatively summing a number of x-ray photons between momentum transfer values $m_1$ and $m_2$ on abscissa 606. A number of x-ray photons that are scattered with momentum transfer values between $m_2$ and $m_3$ are located within a band 630 under graph 624. Processor 190 determines a cumulative number of x-ray photons within band 630 by cumulatively summing a number of x-ray photons between momentum transfer values $m_2$ and $m_3$ on abscissa 606.

Figure 15:
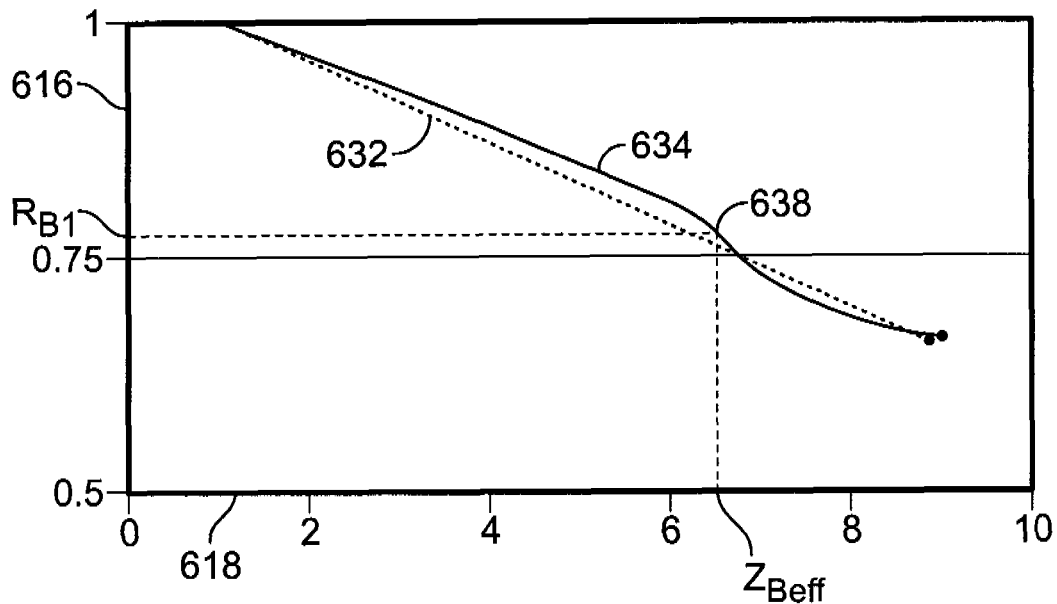
FIG. 15 shows another embodiment of a dotted line and a solid curve generated by the processor.

FIG. 15 shows dotted line 632 and solid curve 634 generated by processor 190. Processor 190 calculates a ratio of cumulative numbers of x-ray photons within bands 628 and 630. For example, processor 190 determines that $R_{B1}$ is a ratio of a cumulative number of x-ray photons within band 628 to a cumulative number of x-ray photons within band 630. Processor 190 determines 636, by using solid curve 634, an effective atomic number $Z_{Beff}$ corresponding to a ratio of a cumulative number of x-ray photons within band 628 and a cumulative number of x-ray photons within band 630. As an example, processor 190 perpendicularly extends a horizontal line from the ratio RB1 to intersect solid curve 634 at an intersection point 638 and extends a line from intersection point 638 to perpendicularly intersect abscissa 616 at an effective atomic number value $Z_{Beff1}$. Alternatively, processor 190 determines, by using dotted line 632, the effective atomic number $Z_{Beff}$ corresponding to a ratio of a cumulative number of x-ray photons within band 628 and a cumulative number of x-ray photons within band 630. As an example, processor 190 perpendicularly extends a horizontal line from the ratio RB1 to intersect dotted line 632 at an intersection point and extends a line from the intersection point to perpendicularly intersect abscissa 616 at an effective atomic number value $Z_{Beff2}$.

Figure 16:
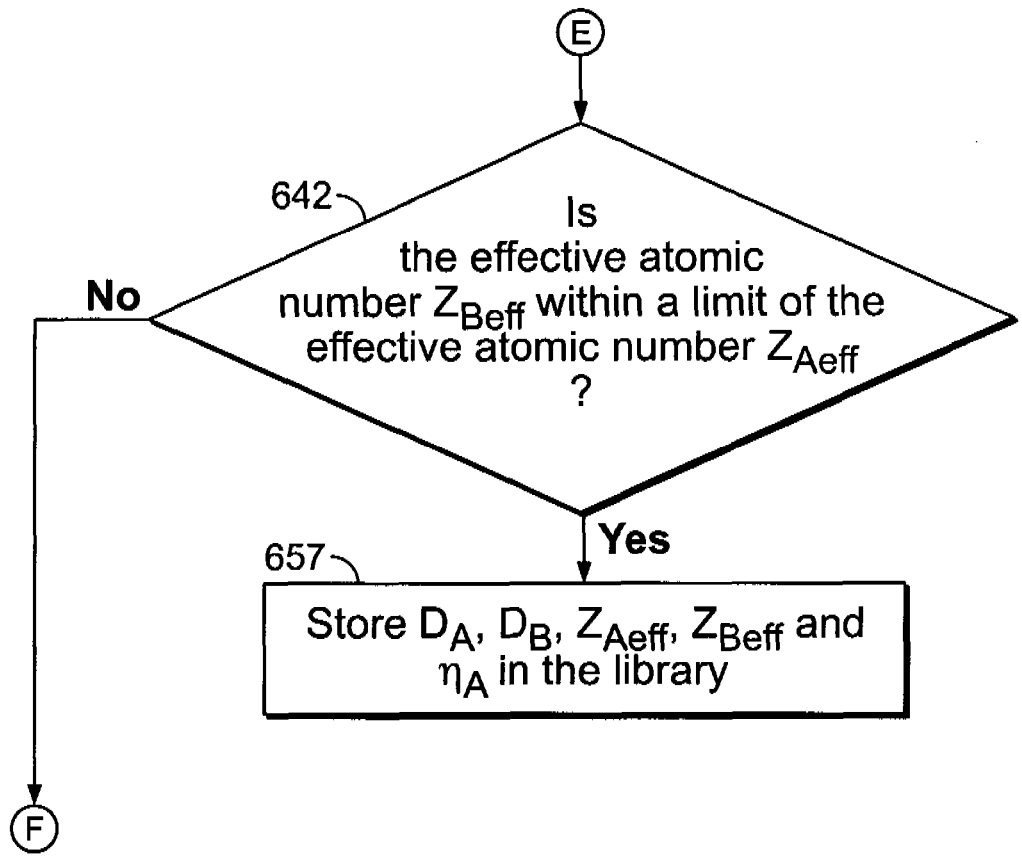
FIG. 16 is a continuation of the flowchart of FIG. 13.

FIG. 16 is a flowchart of an embodiment of a method for identifying a substance. Processor 190 determines 642 whether the effective atomic number $Zeff_B$ is within a limit, such as ranging from and including 0 to 10 percent, of the effective atomic number $Zeff_A$. Upon determining by processor 190 that the effective atomic number $Zeff_B$ is within the limit of the effective atomic number $Zeff_A$, processor 190 stores 657 the effective atomic numbers $Zeff_A$ and $Zeff_B$, and the diffraction profiles $D_A(m)$ and $D_B(m)$, within the library and the user opens container 79 to identify substance 82.

Figure 17:
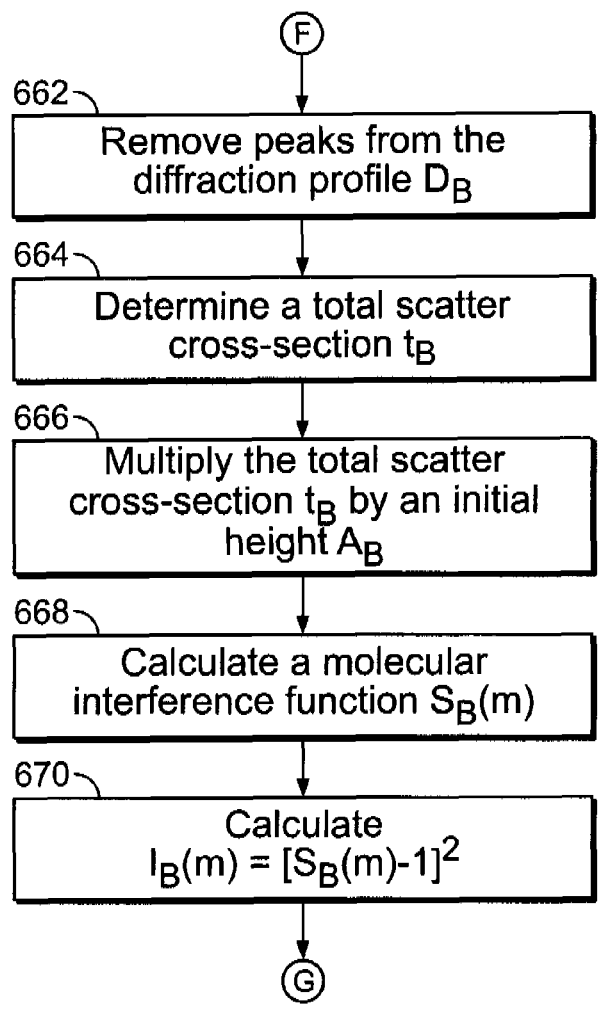
FIG. 17 is a continuation of the flowchart of FIG. 16.
Figure 18:
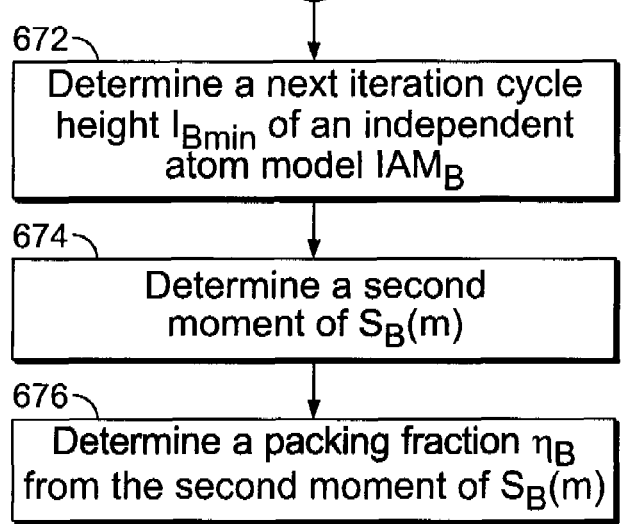
FIG. 18 is a continuation of the flowchart of FIG. 17.
Figure 19:
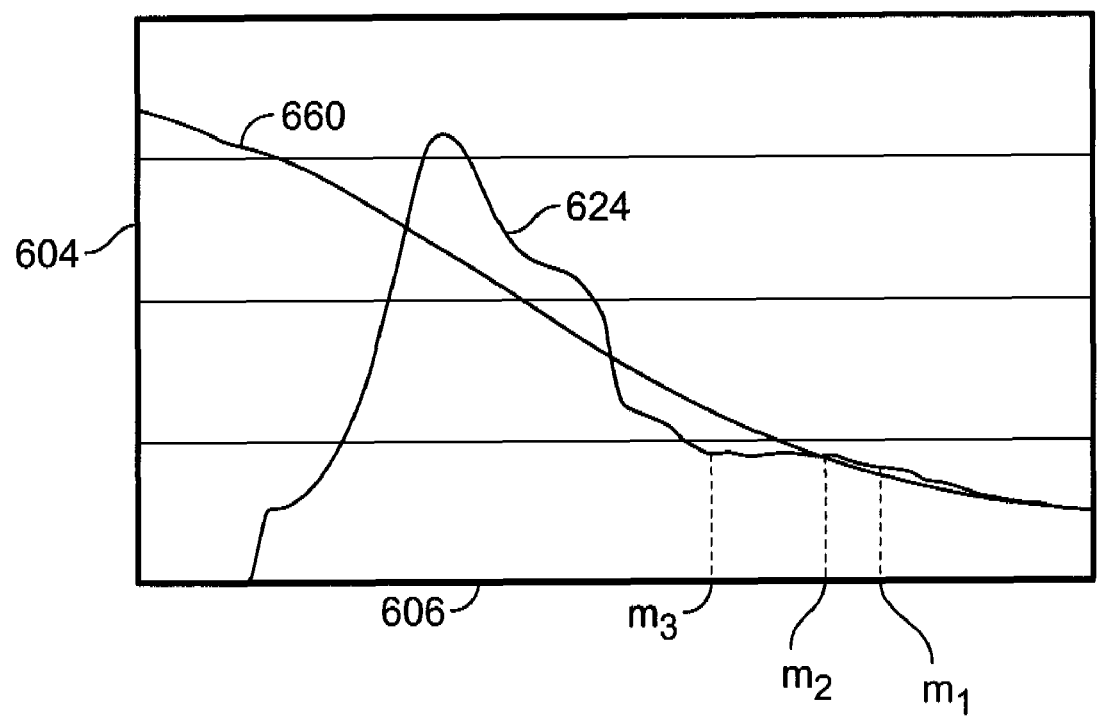
FIG. 19 shows another embodiment of an independent atom model curve generated by the processor.
Figure 20:
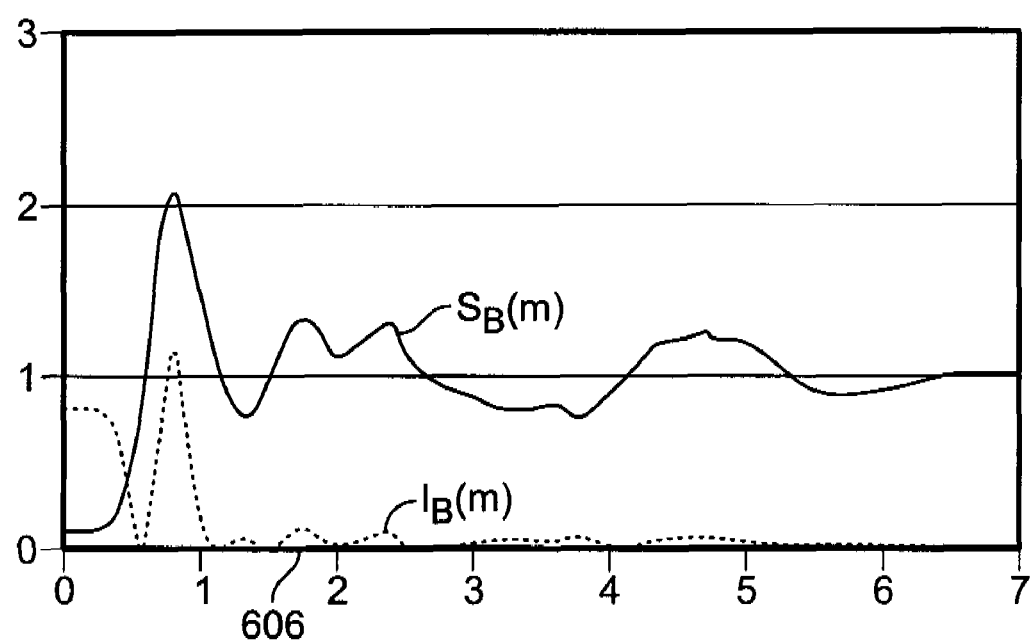
FIG. 20 shows a plurality of embodiments of a plurality of graphs generated by the processor.

FIGS. 17-18 are a flowchart of an embodiment of a method for identifying a substance, FIG. 19 shows an embodiment of an independent atom model ($IAM_B$) curve 660 generated by processor 190, and FIG. 20 shows a plurality of embodiments of a plurality of graphs $S_B(m)$ and $I_B(m)$ generated by processor 190.

The graph $S_B(m)$ represents a molecular interference function and the graph $I_B(m)$ represents an approximation function. Upon determining that the effective atomic number $Zeff_B$ is not within the limit of the effective atomic number $Zeff_A$, processor 190 removes 662 a plurality of crystalline interference peaks from graph 624 by applying the peak removal algorithm. In an alternative embodiment, processor 190 removes all crystalline interference peaks that represents a crystallinity of substance 82 and that are located within the diffraction profile $D_B(m)$ by applying the peak removal algorithm. For example, in case of quasi-amorphous or alternatively partially crystalline substances, a plurality of crystalline interference peaks may be included within graph 624 and processor 190 removes the crystalline interference peaks by applying the peak removal algorithm. The peak removal algorithm is applied to generate a peak-removed graph, such as graph 624.

Processor 190 determines 664 a total scatter cross-section $t_B$ of $IAM_B$ curve 660 from the effective atomic number $Z_{Beff}$. For example, upon determining by processor 190 that the effective atomic number value $Z_{effB1}$ is a second rational number, such as 1.3, processor 190 generates a weighted average $W_B$ of a plurality of $IAM_B$ functions corresponding to neighboring atomic numbers one and two. In the example, processor 190 generates the weighted average $W_B$, such as ⅓[$IAM_B$(1)]+⅔[$IAM_B$(2)], where $IAM_B$(1) is a total scatter cross-section for hydrogen and $IAM_B$(2) is a total scatter cross-section for Helium. An example of the $IAM_B$ functions corresponding to neighboring atomic numbers are available in Hubbell, J. H., Veigele, W. J., Briggs, E. A., Brown, R. T., Cromer, D. T., Howerton, R. J., Atomic Form Factors, Incoherent Scattering Functions and Photon Scattering Cross-sections, Journal of Physics and Chemical Reference Data, Volume 4, page 471 (1975), Erratum: Atomic Form Factors, Incoherent Scattering Functions, and Photon Scattering Cross Sections, Journal of Physics and Chemical Reference Data, Volume 6, page 615 (1977). The weighted average $W_B$ is an example of the total scatter cross-section $t_B$, determined in 664, of $IAM_B$ curve 660.

Alternatively, instead of generating the weighted average $W_B$, upon determining by processor 190 that the effective atomic number value $Z_{Beff1}$ is the second rational number, processor 190 generates a closest total scatter cross-section of $IAM_B$ curve 660 corresponding to an atomic number value, which is an integer closest to the second rational number and plots, with respect to ordinate 604, the closest total scatter cross-section. In yet another alternative embodiment, instead of generating the weighted average $W_B$, upon determining by processor 190 that the effective atomic number value $Z_{Beff1}$ is the second rational number, processor 190 generates a second universal total scatter cross-section of $IAM_B$ curve 660 by scaling the momentum transfer m of $IAM_B$ curve 660. As an example, abscissa 606 is scaled by multiplying the momentum transfer m of $IAM_B$ curve 660 with $0.02Z_{Beff1}+0.12$ to generate the second universal total scatter cross-section of $IAM_B$ curve 660.

Processor 190 multiplies 666 the total scatter cross-section $t_B$, determined in 664, by an initial amplitude $A_B$ or an initial height to generate a first iteration cycle free atom curve $C_B$. For example, processor 190 multiplies each value of a total scatter cross-section $t_B$, determined in 664, with the initial height $A_B$ to generate the first iteration cycle free atom curve $C_B$. Processor 190 receives the initial height $A_B$ from the user via input device 192. Processor 190 calculates 668 the molecular interference function $S_B(m)$ by dividing a number of x-ray photons represented by graph 624 by the first iteration cycle free atom curve $C_B$. As an example, processor 190 generates a molecular interference value $S_{B1}(m)$ of the molecular interference function $S_B(m)$ by dividing a number of x-ray photons having the momentum transfer value $m_1$ that lies on graph 624 by a number of x-ray photons having the momentum transfer value $m_1$ that lies on the first iteration cycle free atom curve $C_B$. As another example, processor 190 generates a molecular interference value $S_{B2}(m)$ of the molecular interference function $S_B(m)$ by dividing a number of x-ray photons having the momentum transfer value $m_2$ that lies on graph 624 by a number of x-ray photons having the momentum transfer value $m_2$ that lies on the first iteration cycle free atom curve $C_B$.

Processor 190 calculates 670 the approximation function $I_B(m)$ as $$I_B(m) = [S_B(m)-1]^2 \tag{7}$$

Processor 190 determines 672 a next iteration cycle amplitude $I_{Bmin}$ or a next iteration cycle height of $IAM_B$ curve 660 by minimizing an integral of $I_B(m)$ represented as $$\int_0^{mmax} I_B(m)dm \tag{8}$$

where $m_{max}$ is the largest value of m on abscissa 606 of graph 624 and $IAM_B$ curve 660. For example, processor 190 determines the next iteration cycle height $I_{Bmin}$ by selecting a minimum from a fourth and a fifth calculated value. Processor 190 determines the fourth calculated value by applying 668, 670, and 672, and equation (8) to the initial height $A_B$. Processor 190 determines the fourth calculated value by applying 666, 668, 670, and equation (8) to a changed height $B_B$ instead of the initial height $A_B$. For example, processor 190 multiplies the total scatter cross-section $t_B$, determined in 664, by the changed height $B_B$ to generate a second iteration cycle free atom curve $C_{SB}$, calculates the molecular interference function $S_B(m)$ by dividing a number of x-ray photons represented by graph 624 by the second iteration cycle free atom curve $C_{SB}$, calculates the approximation function $I_B(m)$ from equation (7), and generates the fourth calculated value by applying equation (8). Processor 190 generates the changed height $B_B$ by modifying, such as incrementing or decrementing, the initial height $A_B$. As another example, processor 190 determines the next iteration cycle height $I_{Bmin}$ by selecting a minimum from a plurality, such as three, of calculated values, such as the fourth calculated value, the fifth calculated value, and a sixth calculated value. Processor 190 generates the sixth calculated value in a similar manner in which fourth and fifth calculated values are generated. For example, processor 190 generates the sixth calculated value after incrementing or alternatively decrementing the changed height $B_B$.

Processor 190 determines 674 a second moment $M2S_B$ of $I_B(m)$ by applying $$M2S_B = \frac{\int_0^\infty m^2 I_{Bmin}(m)dm}{\int_0^\infty I_{Bmin}(m)dm} \tag{9}$$

Processor 190 determines 676 a packing fraction $\eta_B$ of substance 82 as being linearly proportional, such as equal, to the second moment $M2S_B$. The packing fraction $\eta_B$ is linearly proportional to the second moment $M2S_B$ when substance 82 includes a plurality of identical hard spheres over a range of $\eta_B$ of amorphous materials relevant in explosive and/or contraband detection. An example of the linearly proportional relationship includes $$\eta_B = a(M2S_B) \tag{10}$$

Figure 21:
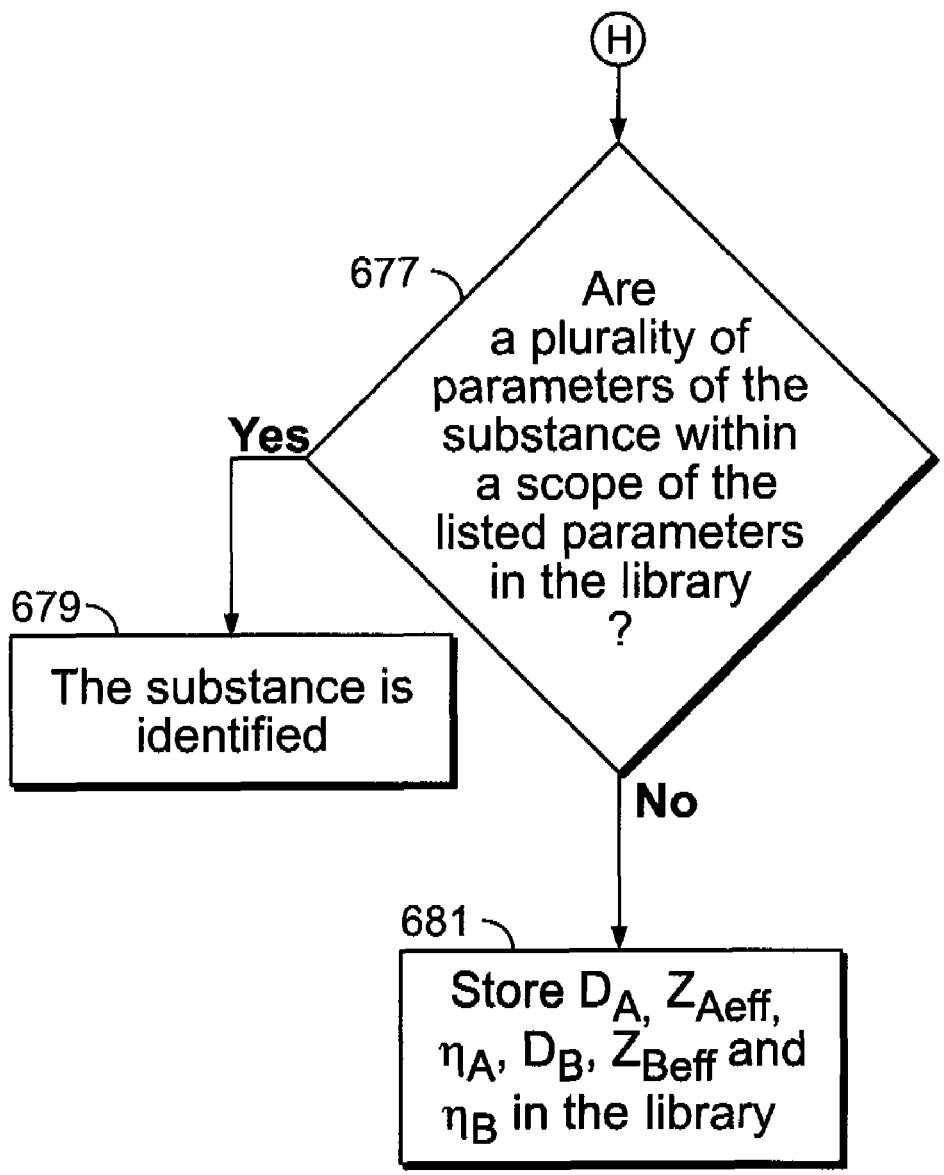
FIG. 21 is a continuation of the flowchart of FIG. 18.

FIG. 21 is a flowchart of an embodiment of a method for identifying a substance. Processor 190 determines 677 whether the diffraction profile $D_B(m)$, the effective atomic number $Z_{Beff}$, and the packing fraction $\eta_B$ are within a scope, such as ranging from and including zero to ten percent, of the sets of listed parameters within a library stored within memory device 195. An example of the determination 677 made by processor 190 includes determining whether the diffraction profile $D_B(m)$ is within the scope of the diffraction profile $D_{II}$, whether the effective atomic number $Z_{Beff}$ is within the scope of the effective atomic number $Z_{IIIeff}$, and the packing fraction $\eta_B$ is within the scope of the packing fraction $\eta_{III}$. Another example of the determination 677 made by processor 190 includes determining whether the diffraction profile $D_B(m)$ is within the scope of the diffraction profile $D_{II}$, whether the effective atomic number $Z_{Beff}$ is within the scope of the effective atomic number $Z_{IIeff}$, and the packing fraction $\eta_B$ is within the scope of the packing fraction $\eta_{II}$. As an example, processor 190 determines whether the diffraction profile $D_B(m)$ is within the scope of the diffraction profile $D_{II}$ by determining whether a number of x-ray photons, plotted on the diffraction profile $D_B(m)$, at the momentum transfer value $m_1$ is within the threshold of a number of x-ray photons, plotted on the diffraction profile $D_{II}$, at the momentum transfer value $m_1$. As another example, processor 190 determines whether the diffraction profile $D_B(m)$ is within the scope of the diffraction profile $D_{II}$ by determining whether a number of x-ray photons, plotted on the diffraction profile $D_B(m)$, at the momentum transfer value $m_2$ is within the scope of a number of x-ray photons, plotted on the diffraction profile $D_{II}$, at the momentum transfer value $m_2$.

Upon determining that the diffraction profile $D_B(m)$, the effective atomic number $Z_{Beff}$, and the packing fraction $\eta_B$ are within the scope of the plurality of listed parameters within the library, processor 190 determines 679 that substance 82 is identified as having one of the sets of listed parameters that are within the scope of the diffraction profile $D_B(m)$, the effective atomic number $Z_{Beff}$, and the packing fraction $\eta_B$. On the other hand, upon determining that the diffraction profile $D_B(m)$, the effective atomic number $Z_{Beff}$, and the packing fraction $\eta_B$ are not within the scope of the plurality of listed parameters within the library, processor 190 stores 681 the diffraction profile $D_A(m)$, the effective atomic number $Z_{Aeff}$, and the packing fraction $\eta_A$, the diffraction profile $D_B(m)$, the effective atomic number $Z_{Beff}$, and the packing fraction $\eta_B$ in the library and the user opens container 79 to identify substance 82.

In an alternative embodiment, processor 190 determines whether at least one of the diffraction profile $D_B(m)$, the effective atomic number $Z_{Beff}$, and the packing fraction $\eta_B$ is within the scope of at least one of the listed parameters within one of the sets of the library. For example, processor 190 determines whether the diffraction profile $D_B(m)$ is within the scope of the diffraction profile $D_H$. As another example, processor 190 determines whether the effective atomic number $Z_{Beff}$ is within the scope of the effective atomic number $Z_{Heff}$. As yet another example, processor 190 determines whether the effective atomic number $Z_{Beff}$ is within the scope of the effective atomic number $Z_{Heff}$ and whether the packing fraction $\eta_B$ is within the scope of the packing fraction $\eta_H$. In the alternative embodiment, upon determining that at least one of the diffraction profile $D_B(m)$, the effective atomic number $Z_{Beff}$, and the packing fraction $\eta_B$ is within the scope of at least one of the listed parameters within one of the sets of the library, processor 190 determines that substance 82 is identified as having the one of the sets of listed parameters having the at least one of the listed parameters within the scope of the at least one of the diffraction profile $D_B(m)$, the effective atomic number $Z_{Beff}$, and the packing fraction $\eta_B$. In the alternative embodiment, processor 190 stores the diffraction profile $D_A(m)$, the effective atomic number $Z_{Aeff}$, and the packing fraction $\eta_A$, the diffraction profile $D_B(m)$, the effective atomic number $Z_{Beff}$, and the packing fraction $\eta_B$ in the library and the user opens container 79 to identify substance 82 upon determining that at least one of the diffraction profile $D_B(m)$, the effective atomic number $Z_{Beff}$, and the packing fraction $\eta_B$ is not within the scope of at least one of the listed parameters within one of the sets of the library.

Figure 22:
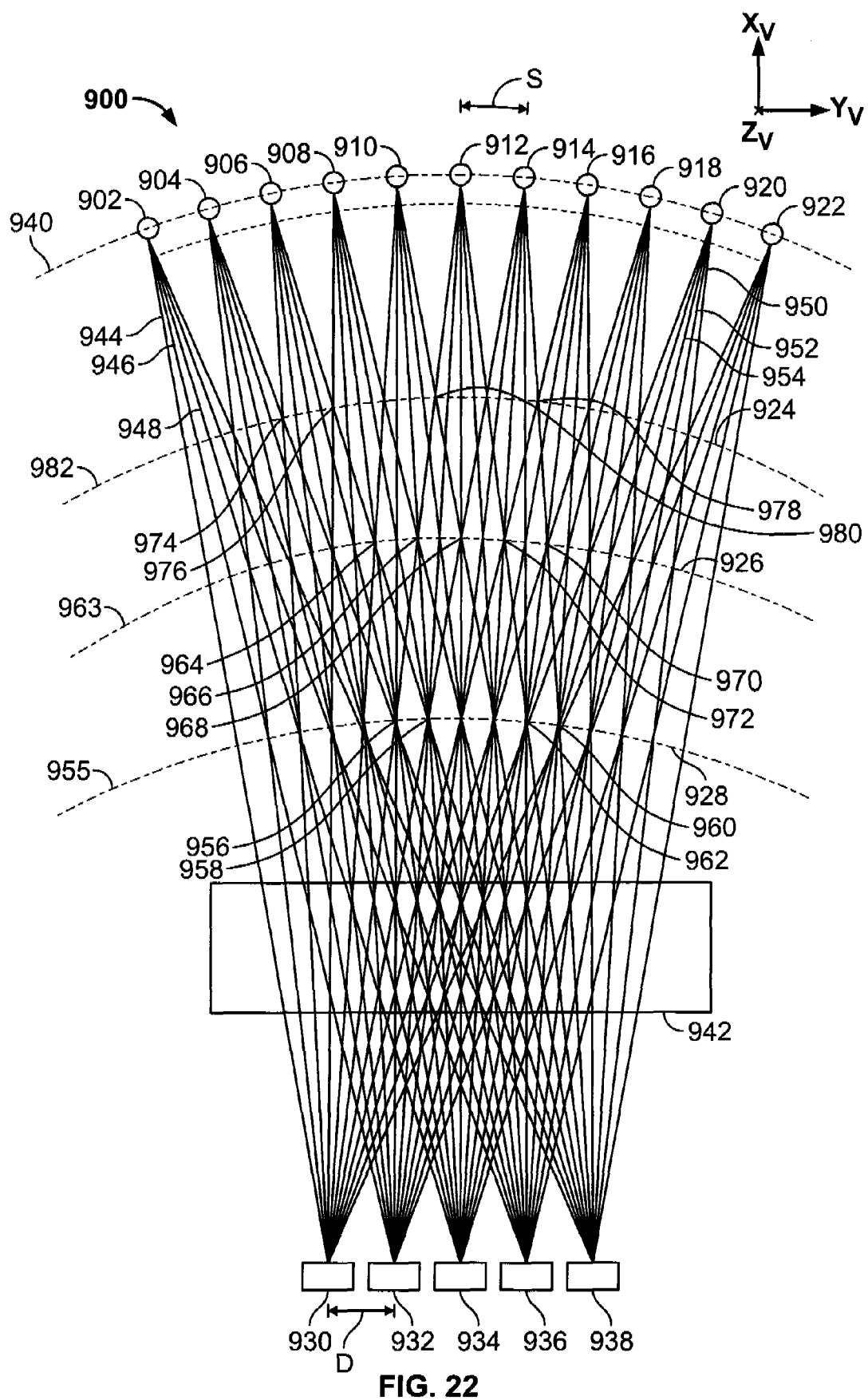
FIG. 22 is a diagram of illustrating an embodiment of a virtual system for developing a primary collimator of the system of FIG. 1.

FIG. 22 is a diagram of illustrating an embodiment of a virtual system 900 for developing a primary collimator. Processor 190 generates virtual system 900. For example, processor 190 generates virtual system 900 to display virtual system 900 on display device 194. Virtual system 900 includes a plurality of virtual x-ray sources 902, 904, 906, 908, 910, 912, 914, 916, 918, 920, and 922, a plurality of virtual collimator elements 924, 926, and 928, and a plurality of virtual detectors 930, 932, 934, 936, and 938, such as virtual transmission detectors. Processor 190 generates virtual x-ray sources 906, 908, 910, 912, 914, 916, 918, and 920 as a virtual representation of x-ray sources 60, 62, 64, 66, 68, 70, 72, and 74 and locates virtual x-ray sources 902, 904, 906, 908, 910, 912, 914, 916, 918, 920, and 922 along a curve 940. Processor 190 generates each of remaining virtual x-ray sources 902, 904, and 922 (FIG. 1) as a virtual representation of an x-ray source, such as x-ray source 74. Moreover, processor 190 generates virtual detector 934 as a virtual representation of transmission detector 17 (FIG. 1). Processor 190 generates each of remaining virtual detectors 930, 932, 936, and 938 as a virtual representation of a transmission detector, such as transmission detector 17. Processor 190 generates a virtual opening 942 as a virtual representation of opening 65 (FIG. 1).

The user provides an organization of the components of system 10 (FIG. 1) to processor 190 via input device 192. The user inputs, via input device 192, a plurality of distances between the components of system and provides the organization of the components of system 107 to processor 190 by providing the distances to processor 190 via input device 192. For example, the user specifies a number of detector elements within transmission detector 17, a number of detector elements within each of scatter detectors 16 and 18, a radius of arc 75, a plurality of positions of x-ray sources 60, 62, 64, 66, 68, 70, 72, and 74 with respect to at least one of transmission detector 17, scatter detector 16, and scatter detector 18, a distance between any two of x-ray sources 60, 62, 64, 66, 68, 70, 72, and 74, and a position of opening 65 with respect to at least one of transmission detector 17, scatter detector 16, and scatter detector 18, and x-ray source 66.

Processor 190 organizes the virtual elements of virtual system 900 and the organization is proportional, by a first factor, such as one-half or one-third, to the organization of the components of system 107 input by the user. For example, processor 190 generates any two of adjacent virtual x-ray sources from virtual x-ray sources 902, 904, 906, 908, 910, 912, 914, 916, 918, 920, and 922 and a distance between the two adjacent virtual x-ray sources is proportional, such as one-half or one-third, to a distance between any two adjacent x-ray sources from x-ray sources 60, 62, 64, 66, 68, 70, 72, and 74. As another example, processor 190 generates two adjacent virtual detectors from virtual detectors 930, 932, 934, 936, and 938 and a distance between the two adjacent virtual detectors is proportional to a distance between transmission detector 17 (FIG. 1) and another transmission detector (not shown) adjacent to transmission detector 17 (FIG. 1). As yet another example, processor 190 generates virtual x-ray source 912 and virtual detector 934, and a distance between virtual x-ray source 912 and virtual detector 934 is proportional to a distance between x-ray source 66 and transmission detector 17. As still another example, processor 190 generates virtual opening 942 and a distance between virtual opening 942 and virtual x-ray source 912 is proportional to a distance between x-ray source 66 and opening 65. As a further example, processor 190 generates virtual detector 934 and a distance between virtual detector 934 and virtual opening 942 is proportional to a distance between transmission detector 17 and opening 65.

Processor 190 extends a number, such as four or five, of virtual beams, which are straight lines, from each virtual x-ray source 902, 904, 906, 908, 910, 912, 914, 916, 918, 920, and 922. Processor 190 extends the number of virtual beams and the number matches a number of virtual detectors 930, 932, 934, 936, and 938. For example, processor 190 extends five virtual beams from each virtual x-ray source 902, 904, 906, 908, 910, 912, 914, 916, 918, 920, and 922 and upon organizing five virtual detectors 930, 932, 934, 936, and 938 within virtual system 900. As another example, processor 190 extends four virtual beams from each virtual x-ray source 902, 904, 906, 908, 910, 912, 914, 916, 918, 920, and 922 and upon organizing four virtual detectors within virtual system 900.

Processor 190 extends the number of virtual beams from each virtual x-ray source 902, 904, 906, 908, 910, 912, 914, 916, 918, 920, and 922 and each virtual detector 930, 932, 934, 936, and 938 receives one of the virtual beams. For example, processor 190 extends a virtual beam 944, as a straight line, from virtual x-ray source 902 and virtual detector 930 receives virtual beam 944. As another example, processor 190 extends a virtual beam 946, as a straight line, from virtual x-ray source 902 and virtual detector 932 receives virtual beam 946. As yet another example, processor 190 extends a virtual beam 948, as a straight line, from virtual x-ray source 902 and virtual detector 934 receives virtual beam 948. As still another example, processor 190 extends a virtual beam 950, as a straight line, from virtual x-ray source 920 and processor 190 and virtual detector 938 receives virtual beam 950. As another example, processor 190 extends a virtual beam 952, as a straight line, from virtual x-ray source 920 and virtual detector 936 receives virtual beam 952. As yet another example, processor 190 extends a virtual beam 954, as a straight line, from virtual x-ray source 920 and virtual detector 934 receives virtual beam 954.

Processor 190 determines a number of virtual points between virtual x-ray sources 902, 904, 906, 908, 910, 912, 914, 916, 918, 920, and 922 and virtual detectors 930, 932, 934, 936, and 938 and a maximum number, such as 5 or 6, of virtual beams intersect each other at each of the virtual points. As an example, processor 190 determines that five virtual beams from virtual x-ray sources 904, 906, 908, 910, and 912 intersect each other at a virtual point 956. As another example, processor 190 determines that five virtual beams from virtual x-ray sources 906, 908, 910, 912, and 914 intersect each other at a virtual point 958. The maximum number is equal to the number of virtual beams output by each virtual x-ray source 902, 904, 906, 908, 910, 912, 914, 916, 918, 920, and 922. Similarly, processor 190 determines virtual points 960 and 962. Processor 190 generates an axis 955 that extends through virtual points 956, 958, 960, and 962. Processor 190 generates virtual collimator element 928 that coincides with axis 955 at a plurality of virtual points, such as virtual points 956, 958, 960, and 962. In an alternative embodiment, processor 190 generates a lower or alternatively a higher number of virtual points on axis 955 than a number of virtual points 956, 958, 960, and 962.

Processor 190 determines a number of virtual points between virtual x-ray sources 902, 904, 906, 908, 910, 912, 914, 916, 918, 920, and 922 and virtual detectors 930, 932, 934, 936, and 938 and a number, such as three, lower than the maximum number, of virtual beams intersect each other at each of the virtual points. As an example, processor 190 determines that three virtual beams from virtual x-ray sources 906, 908, and 910 intersect each other at a virtual point 964. As another example, processor 190 determines that three virtual beams from virtual x-ray sources 908, 910, and 912 intersect each other at a virtual point 966. Similarly, processor 190 determines virtual points 968, 970, and 972. Processor 190 generates an axis 963 that extends through virtual points 964, 966, 968, 970, and 972. Processor 190 generates virtual collimator element 926 that coincides with axis 963 at a plurality of virtual points, such as virtual points 964, 966, 968, 970, and 972. As yet another example, processor 190 determines that two virtual beams from virtual x-ray sources 904 and 906 intersect each other at a virtual point 974. As another example, processor 190 determines that two virtual beams from virtual x-ray sources 906 and 908 intersect each other at a virtual point 976. Similarly, processor 190 determines virtual points 978 and 980. Processor 190 generates an axis 982 that extends through virtual points 974, 976, 978, and 980. Processor 190 collates the intersection points to find those which pass through approximately the same x-position. Processor 190 generates virtual collimator element 924 that coincides with axis 982 at a plurality of virtual points, such as virtual points 974, 976, 978, and 980. Virtual collimator element 928 is closest to virtual opening 942 than the remaining virtual collimator elements 924 and 926. In an alternative embodiment, processor 190 generates a lower or alternatively a higher number of virtual points on axis 963 than a number of virtual points 964, 966, 968, 970, and 972. In another alternative embodiment, 190 generates a lower or alternatively a higher number of virtual points on axis 982 than a number of virtual points 974, 976, 978, and 980.

Processor 190 generates virtual collimator elements 924, 926, and 928 and virtual collimator elements 924, 926, and 928 do not intersect virtual opening 942. In an alternative embodiment, virtual collimator elements 924, 926, and 928 do not intersect container 79. Processor 190 generates virtual collimator elements 924, 926, and 928 that lie between virtual x-ray sources 902, 904, 906, 908, 910, 912, 914, 916, 918, 920, and 922 and virtual opening 942. Processor 190 determines a plurality of virtual positions, such as $x_{v1}$ and $y_{v1}$ virtual co-ordinates or $x_{v2}$ and $y_{v2}$ virtual co-ordinates or $x_{v3}$ and $y_{v3}$ virtual co-ordinates, of virtual collimator elements 924, 926, and 928 and determines a plurality of positions, such as $xv_4$ and $y_{v4}$ virtual co-ordinates, $xv_5$ and $y_{v5}$ virtual co-ordinates, $xv_6$ and $y_{v6}$ virtual co-ordinates, $x_{v7}$ and $y_{v7}$ virtual co-ordinates, $x_{v8}$ and $y_{v8}$ virtual co-ordinates, or $x_{v9}$ and $y_{v9}$ virtual co-ordinates, of virtual points on virtual collimator elements 924, 926, and 928. For example, processor 190 determines the $x_{v1}$ and $y_{v1}$ virtual co-ordinates of virtual collimator element 928 with respect to an origin of an $x_v y_v z_v$ co-ordinate system. As another example, processor 190 determines the $x_{v4}$ and $y_{v4}$ virtual co-ordinates of virtual point 974 with respect to the origin of the $x_v y_v z_v$ co-ordinate system. The $x_v y_v z_v$ co-ordinate system is proportional to the xyz co-ordinate system shown in FIGS. 1, 4, and 5. The $x_v y_v z_v$ co-ordinate system includes an $x_v$ axis, a $y_v$ axis, and a $z_v$ axis. The $x_v$ axis is perpendicular to the $y_v$ axis and the $z_v$ axis, and the $y_v$ axis is perpendicular to the $z_v$ axis.

It is noted that virtual collimator elements 924, 926, and 928 are curved and that none of virtual collimator elements 924, 926, and 928 are circular in shape. It is also noted that in an alternative embodiment, processor 190 generates virtual collimator element 928 and does not generate any other virtual collimator element. In yet another alternative embodiment, processor 190 generates any number, such as 2, 3, 4, or 5, of virtual collimator elements.

Figure 23:
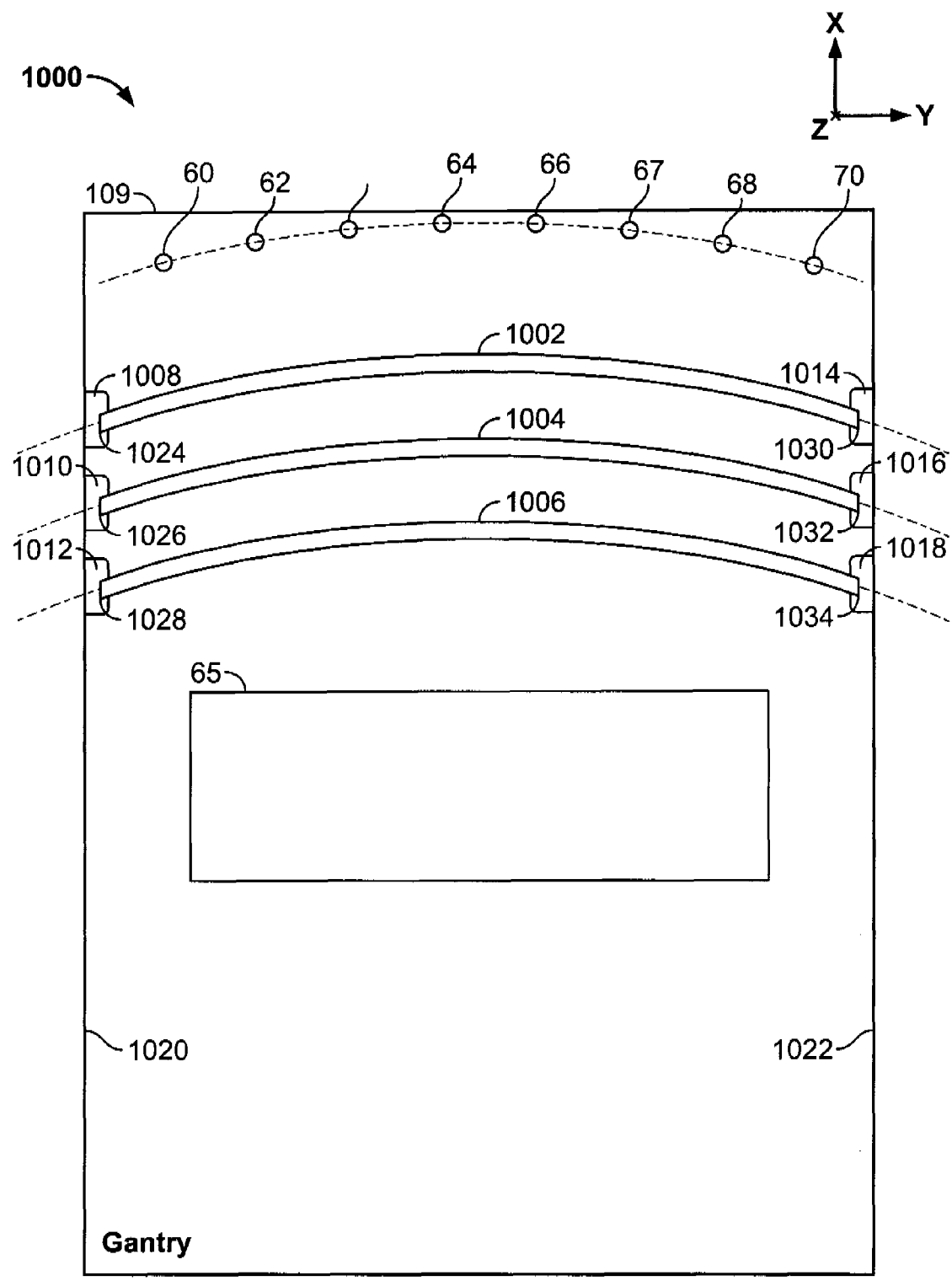
FIG. 23 is a diagram of an embodiment of a system implementing the primary collimator.

FIG. 23 is a diagram of an embodiment of a system 1000 implementing a primary collimator. System 1000 is an example of system 107 (FIG. 2). System 1000 includes gantry 109 (FIG. 2). Gantry 109 includes opening 65, x-ray sources 60, 62, 64, 66, 68, 70, 72, and 74, a plurality of primary collimator elements 1002, 1004, and 1006, and a plurality of holders 1008, 1010, 1012, 1014, 1016, and 1018. An example of each of primary collimator elements 1002, 1004, and 1006 include a sheet or a lamination. Primary collimator elements 1002, 1004, and 1006 are fabricated from a material, such as molybdenum or tungsten. Holders 1008, 1010, 1012, 1014, 1016, and 1018 are fabricated from a metal, such as steel or aluminum. Primary collimator elements 1002, 1004, and 1006 are located between x-ray sources 60, 62, 64, 66, 68, 70, 72, and 74 and opening 65, and collectively form primary collimator 14 (FIG. 1). As an example, each primary collimator element 1002, 1004, and 1006 has a length ranging from and including 1 meters (m) to 1.5 meters in the y-direction, ranging from and including 0.5 millimeters (mm) to 5 mm in the z-direction, and ranging from and including 2.5 mm to 5.5 mm in the x-direction.

Primary collimator element 1002 is supported by holders 1008 and 1014. Primary collimator element 1004 is support by holders 1010 and 1016, and primary collimator element 1006 is supported by holders 1012 and 1018. Holders 1008, 1010, 1012, 1014, 1016, and 1018 are attached by a connection process, such as gluing or spot welding, to a plurality of side walls 1020 and 1022 of gantry 109 (FIG. 2). For example, holders 1008, 1010, and 1012 are attached to side wall 1020 and holders 1014, 1016, and 1018 are attached to side wall 1022. Alternatively, holders 1008, 1010, 1012, 1014, 1016, and 1018 are attached to side walls 1020 and 1022 by fitting holders 1008, 1010, and 1012 to side wall 1020 via a plurality of screws and by fitting holders 1014, 1016, and 1018 to side wall 1022 via a plurality of screws. Each of holders 1008, 1010, 1012, 1014, 1016, and 1018 include a slot that extends in the z-direction. For example, holder 1008 includes a slot 1024, holder 1010 includes a slot 1026, holder 1012 includes a slot 1028, holder 1014 includes a slot 1030, holder 1016 includes a slot 1032, and holder 1018 includes a slot 1034.

The user fabricates holders 1008, 1010, 1012, 1014, 1016, and 1018 and slots 1024, 1026, 1028, 1030, 1032, and 1034 by using a molding machine having a plurality of peaks of a shape of any of slots 1024, 1026, 1028, 1030, 1032, and 1034, filling a liquid metal, such as steel, within the molding machine, and cooling the metal to create slots 1024, 1026, 1028, 1030, 1032, and 1034 within holders 1008, 1010, 1012, 1014, 1016, and 1018. Alternatively, the user creates slots 1024, 1026, 1028, 1030, 1032, and 1034 by operating an etching machine to develop slots 1024, 1026, 1028, 1030, 1032, and 1034. Each of slots 1024, 1026, 1028, 1030, 1032, and 1034 have a plurality of dimensions that are slightly larger than a plurality of dimensions of each of primary collimator elements 1002, 1004, and 1006. For example, if primary collimator element 1002 has a dimension along the x-axis of 5 mm, slot 1024 has a dimension along the x-axis of more than 5 mm, such as 5.2 mm. As another example, if primary collimator element 1002 has a dimension along the y-axis of 1.2 m, slot 1024 has a dimension along the y-axis of more than 1.2 m, such as 1.5 m. As yet another example, if primary collimator element 1002 has a dimension along the z-axis of 1 mm, slot 1024 has a dimension along the y-axis of more than 1.2 mm, such as 1.5 mm.

The user slides a primary collimator element within slots to use holders to support primary collimator element. For example, the user slides, in the z-direction, primary collimator element 1002 within slot 1024 of holder 1008 and slot 1030 of holder 1014 to use holders 1008 and 1014 to support primary collimator element 1002. As another example, the user slides, in the z-direction, primary collimator element 1004 within slot 1026 of holder 1010 and slot 1032 of holder 1016 to use holders 1010 and 1016 to support primary collimator element 1004.

Processor 190 calculates a plurality of positions, such as $x_1$ and $y_1$ co-ordinates, $x_2$ and $y_2$ co-ordinates, or $x_3$ and $y_3$ co-ordinates, of primary collimator elements 1002, 1004, and 1006 within gantry 109 as being proportional, by a second factor, such as 2 or 3, to the virtual positions of virtual collimator elements 924, 926, and 928. For example, processor 190 multiplies the co-ordinates $x_{v1}$ and $y_{v1}$ co-ordinates of virtual collimator element 928 with the second factor to generate the $x_1$ and $y_1$ co-ordinates of primary collimator element 1006. As another example, processor 190 multiplies the $x_{v2}$ and $y_{v2}$ co-ordinates of virtual collimator element 926 with the second factor to generate the $x_2$ and $y_2$ co-ordinates of primary collimator element 1004. As yet another example, processor 190 multiplies the $x_{v3}$ and $y_{v3}$ co-ordinates of virtual collimator element 924 with the second factor to generate the co-ordinates $x_3$ and $y_3$ of primary collimator element 1002. The second factor is an inverse of the first factor. For example, if the first factor is one-half, the second factor is 2.

Virtual collimator element 924 (FIG. 22) is a virtual representation of primary collimator element 1002, virtual collimator element 926 (FIG. 22) is a virtual representation of primary collimator element 1004, and virtual collimator element 928 (FIG. 22) is a virtual representation of primary collimator element 1006. Primary collimator 14 includes any number, such as 2, 3, or 4, of primary collimator elements, such as primary collimator elements 1002, 1004, and 1006. Primary collimator element 1006 has a minimum number of apertures compared to a number of apertures in either primary collimator element 1002 or primary collimator element 1004. It is advantageous to have primary collimator element 1006 with the minimum number of apertures. The minimum number of apertures depends on a size of container 79 and a number of x-ray sources for scanning container 79.

Figure 24:
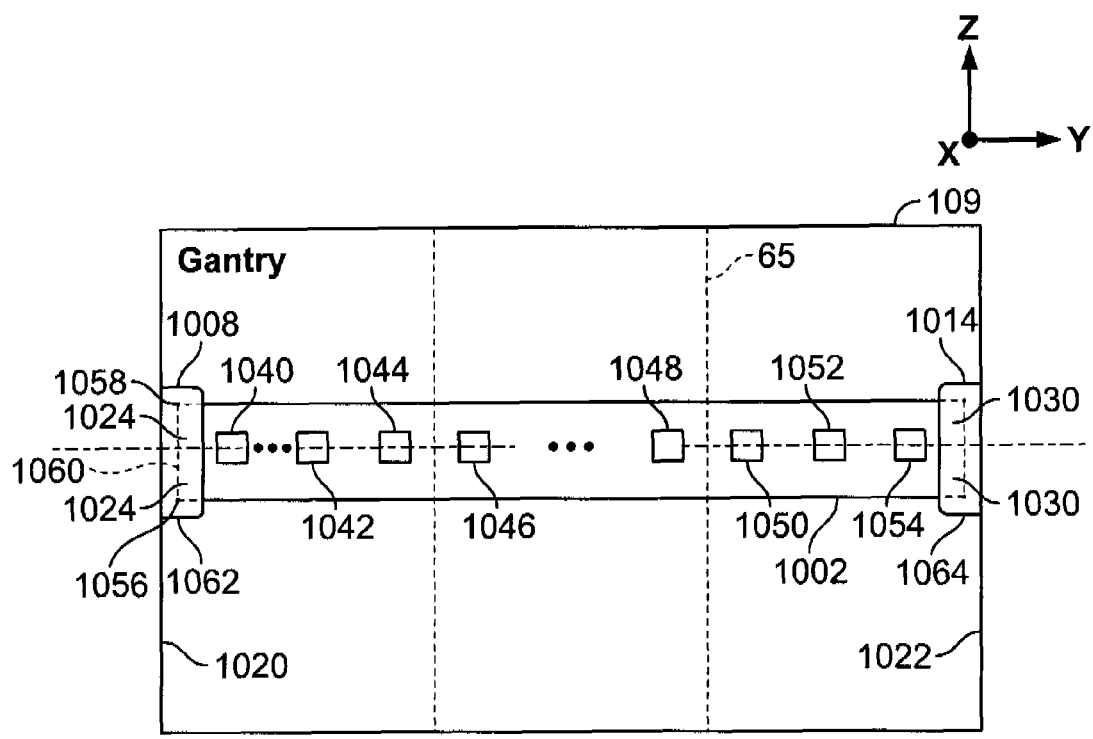
FIG. 24 is a top view of an embodiment of a gantry of the system of FIG. 1.

FIG. 24 is a top view of an embodiment of gantry 109 (FIG. 2). Gantry 109 includes primary collimator element 1002 and holders 1008 and 1014. Primary collimator element 1002 includes a plurality of apertures 1040, 1042, 1044, 1046, 1048, 1050, 1052, and 1054. A number of apertures within primary collimator element 1002 is equal to a number of virtual points on virtual collimator element 924. Processor 190 outputs a plurality of positions, such as the co-ordinates $x_4$ and $y_4$, of apertures within primary collimator element 1002 as being proportional by the second factor to the positions of virtual points of virtual collimator element 924. For example, processor 190 multiplies the virtual co-ordinates $x_{v4}$ and $y_{v4}$ of virtual point 974 with the second factor to generate the co-ordinates $x_4$ and $y_4$ of aperture 1042 of primary collimator element 1002. As another example, processor 190 multiplies the co-ordinates $x_{v5}$ and $y_{v5}$ of virtual point 976 with the second factor to generate a plurality of co-ordinates $x_5$ and $y_5$ of aperture 1044 of primary collimator element 1002.

Slot 1024 has a length in the z-direction greater than a length of primary collimator element 1002 in the z-direction. For example, slot 1024 extends, within holder 1008, from a point 1056 to a point 1058, along the z-direction and primary collimator element 1002 extends from a point 1060 to point 1058, along the z-direction. A distance, in the z-direction, between points 1058 and 1060 is less than a distance, in the z-direction, between points 1056 and 1058. The user slides, in the z-direction, primary collimator element 1002 from a side 1062 of holder 1008 into slot 1024 and from a side 1064 of holder 1014 into slot 1030 to locate primary collimator element 1002 within slots 1024 and 1030.

Figure 25:
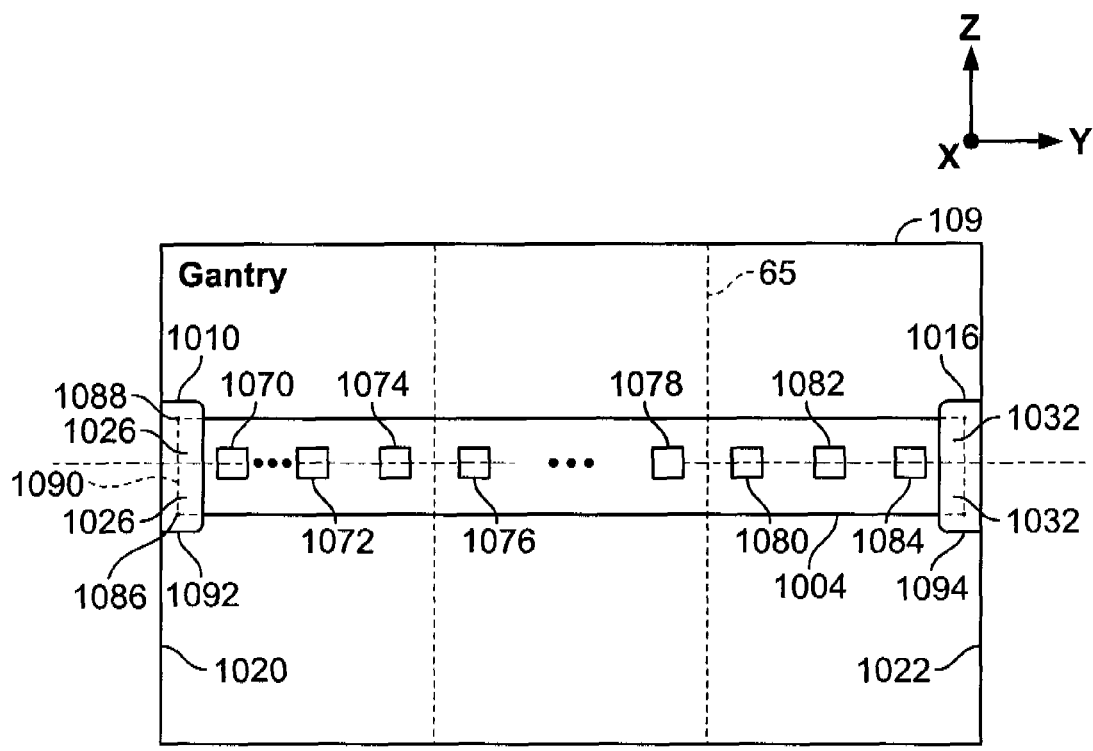
FIG. 25 is another top view of an embodiment of the gantry.

FIG. 25 is a top view of an embodiment of gantry 109 (FIG. 2). Gantry 109 includes primary collimator element 1004 and holders 1010 and 1016. Primary collimator element 1004 includes a plurality of apertures 1070, 1072, 1074, 1076, 1078, 1080, 1082, and 1084. A number of apertures within primary collimator element 1004 is equal to a number of virtual points on virtual collimator element 926. Processor 190 outputs a plurality of positions, such as the co-ordinates $x_6$ and $y_6$, of apertures 1070, 1072, 1074, 1076, 1078, 1080, 1082, and 1084 within primary collimator element 1004 as being proportional by the second factor to the virtual positions of virtual points of virtual collimator element 926 (FIG. 22). For example, processor 190 multiplies the virtual co-ordinates $x_{v6}$ and $y_{v6}$ of virtual point 964 (FIG. 22) with the second factor to generate the co-ordinates $x_6$ and Y6 of aperture 1074 of primary collimator element 1004. As another example, processor 190 multiplies the co-ordinates $x_{v7}$ and $y_{v7}$ of virtual point 966 (FIG. 22) with the second factor to generate a plurality of co-ordinates $x_7$ and $y_7$ of aperture 1076 of primary collimator element 1004.

Slot 1026 has a length in the z-direction greater than a length of primary collimator element 1004 in the z-direction. For example, slot 1026 extends, within holder 1010, from a point 1086 to a point 1088, along the z-direction and primary collimator element 1004 extends from a point 1090 to point 1088, along the z-direction. A distance, in the z-direction, between points 1088 and 1090 is less than a distance, in the z-direction, between points 1086 and 1088. The user slides, in the z-direction, primary collimator element 1004 from a side 1092 of holder 1010 into slot 1026 and from a side 1094 of holder 1016 into slot 1032 to locate primary collimator element 1004 within slots 1026 and 1032.

Figure 26:
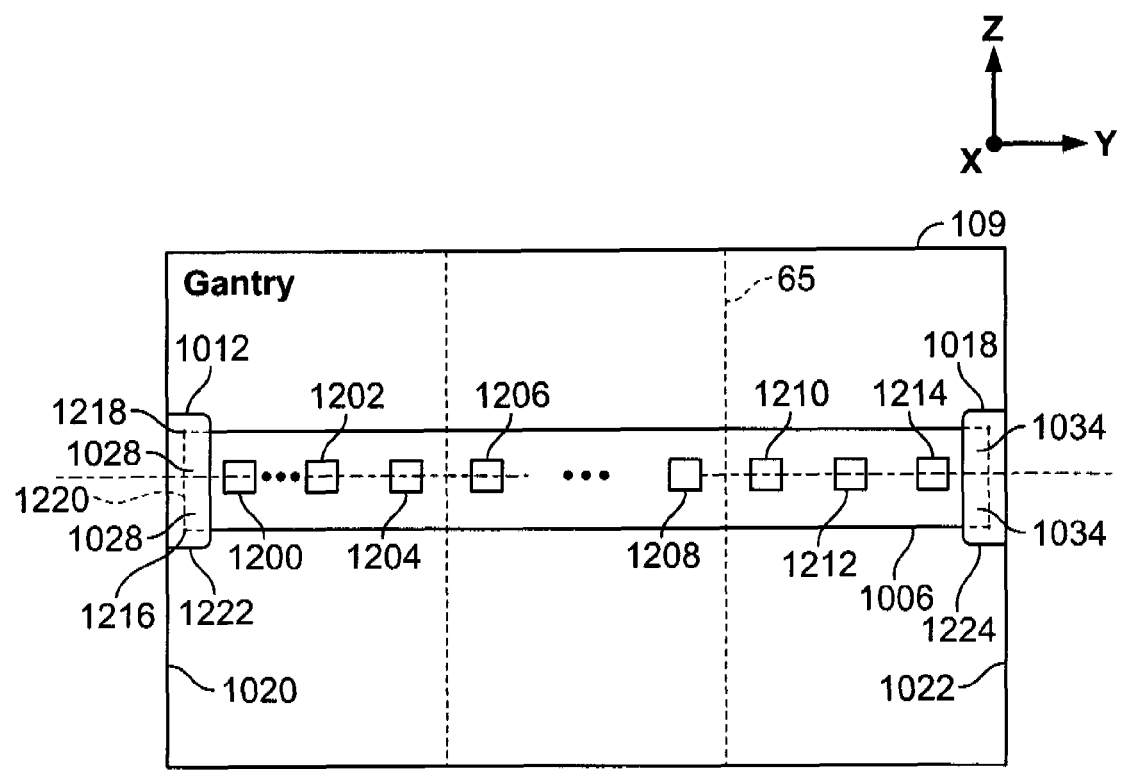
FIG. 26 is yet another top view of an embodiment of the gantry.

FIG. 26 is a top view of an embodiment of gantry 109 (FIG. 2). Gantry 109 includes primary collimator element 1006 and holders 1012 and 1018. Primary collimator element 1006 includes a plurality of apertures 1200, 1202, 1204, 1206, 1208, 1210, 1212, and 1214. A number of apertures within primary collimator element 1006 is equal to a number of virtual points on virtual collimator element 928. Processor 190 outputs a plurality of positions, such as the co-ordinates $x_8$ and $y_8$, of apertures 1200, 1202, 1204, 1206, 1208, 1210, 1212, and 1214 within primary collimator element 1006 as being proportional by the second factor to the virtual positions of virtual points of virtual collimator element 928. For example, processor 190 multiplies the virtual co-ordinates $x_{v8}$ and $y_{v8}$ of virtual point 956 with the second factor to generate the co-ordinates $x_8$ and $y_8$ of aperture 1202 of primary collimator element 1006. As another example, processor 190 multiplies the co-ordinates $x_{v9}$ and $y_{v9}$ of virtual point 958 with the second factor to generate a plurality of co-ordinates $x_9$ and $y_9$ of aperture 1204 of primary collimator element 1006.

Slot 1028 has a length in the z-direction greater than a length of primary collimator element 1006 in the z-direction. For example, slot 1028 extends, within holder 1012, from a point 1216 to a point 1218, along the z-direction and primary collimator element 1006 extends from a point 1220 to point 1218, along the z-direction. A distance, in the z-direction, between points 1218 and 1220 is less than a distance, in the z-direction, between points 1216 and 1218. The user slides, in the z-direction, primary collimator element 1006 from a side 1222 of holder 1012 into slot 1028 and a side 1224 of holder 1018 into slot 1034 to locate primary collimator element 1006 within slots 1028 and 1034.

The user creates apertures 1040, 1042, 1044, 1046, 1048, 1050, 1052, 1054, 1070, 1072, 1074, 1076, 1078, 1080, 1082, 1084, 1200, 1202, 1204, 1206, 1208, 1210, 1212, and 1214 by applying a process, such as a molding process. For example, the user creates apertures 1040, 1042, 1044, 1046, 1048, 1050, 1052, and 1054 of primary collimator element 1002 by using a molding machine having a plurality of peaks of a shape of any of apertures 1040, 1042, 1044, 1046, 1048, 1050, 1052, and 1054, filling a metal, such as tungsten or molybdenum, within the molding machine, and cooling the metal to create apertures 1040, 1042, 1044, 1046, 1048, 1050, 1052, and 1054. As an example, each aperture 1040, 1042, 1044, 1046, 1048, 1050, 1052, 1054, 1070, 1072, 1074, 1076, 1078, 1080, 1082, 1084, 1200, 1202, 1204, 1206, 1208, 1210, 1212, and 1214 has a width ranging from and including 0.5 mm to 1.5 mm in the y-direction, a depth ranging from and including 0.1 mm to 0.5 mm in the z-direction, and a thickness ranging from and including 2.5 mm to 5.5 mm in the x-direction. A thickness of each aperture in the x-direction is the same as a thickness, in the x-direction, of a primary collimator element that includes the aperture. For example, a thickness of aperture 1040 in the x-direction is the same as a thickness of primary collimator element 1002 in the x-direction. The user creates apertures 1040, 1042, 1044, 1046, 1048, 1050, 1052, 1054, 1070, 1072, 1074, 1076, 1078, 1080, 1082, 1084, 1200, 1202, 1204, 1206, 1208, 1210, 1212, and 1214 as having the same location, along the z-axis, as that of x-ray sources 60, 62, 64, 66, 68, 70, 72, and 74 (FIG. 1) along the z-axis.

When x-ray beam 67 (FIG. 1) passes through primary collimator 14, primary collimator 14 collimates x-ray beam 67 to generate primary beams 83 and 84 (FIG. 1) from two apertures 1046 and 1048 (FIG. 8), respectively. Alternatively or in addition, when x-ray beam 67 (FIG. 1) passes through primary collimator 14, primary collimator 14 collimates x-ray beam 67 to generate primary beams 83 and 84 (FIG. 1) from two apertures 1076 and 1078, respectively. Moreover, alternatively or in addition, when x-ray beam 67 (FIG. 1) passes through primary collimator 14, primary collimator 14 collimates x-ray beam 67 to generate primary beams 83 and 84 (FIG. 1) from two apertures 1206 and 1208, respectively. Each aperture outputs a primary beam. For example, aperture 1072 outputs a primary beam. As another example, aperture 1200 outputs a primary beam.

It is noted that an additional primary collimator element (not shown) is included within primary collimator 14 and coincides with points corresponding to a plurality of virtual points other than virtual points at which at least two beams from virtual x-ray sources 902, 904, 906, 908, 910, 912, 914, 916, 918, 920, and 922 intersect. The additional primary collimator element is parallel to any one of primary collimator elements 1002, 1004, and 1006 and includes a plurality of apertures to allow x-rays from x-ray sources 60, 62, 64, 66, 68, 70, 72, and 74 to reach any of primary collimator elements 1002, 1004, and 1006. In an alternative embodiment, primary collimator 14 does not include the additional primary collimator element.

Figure 27:
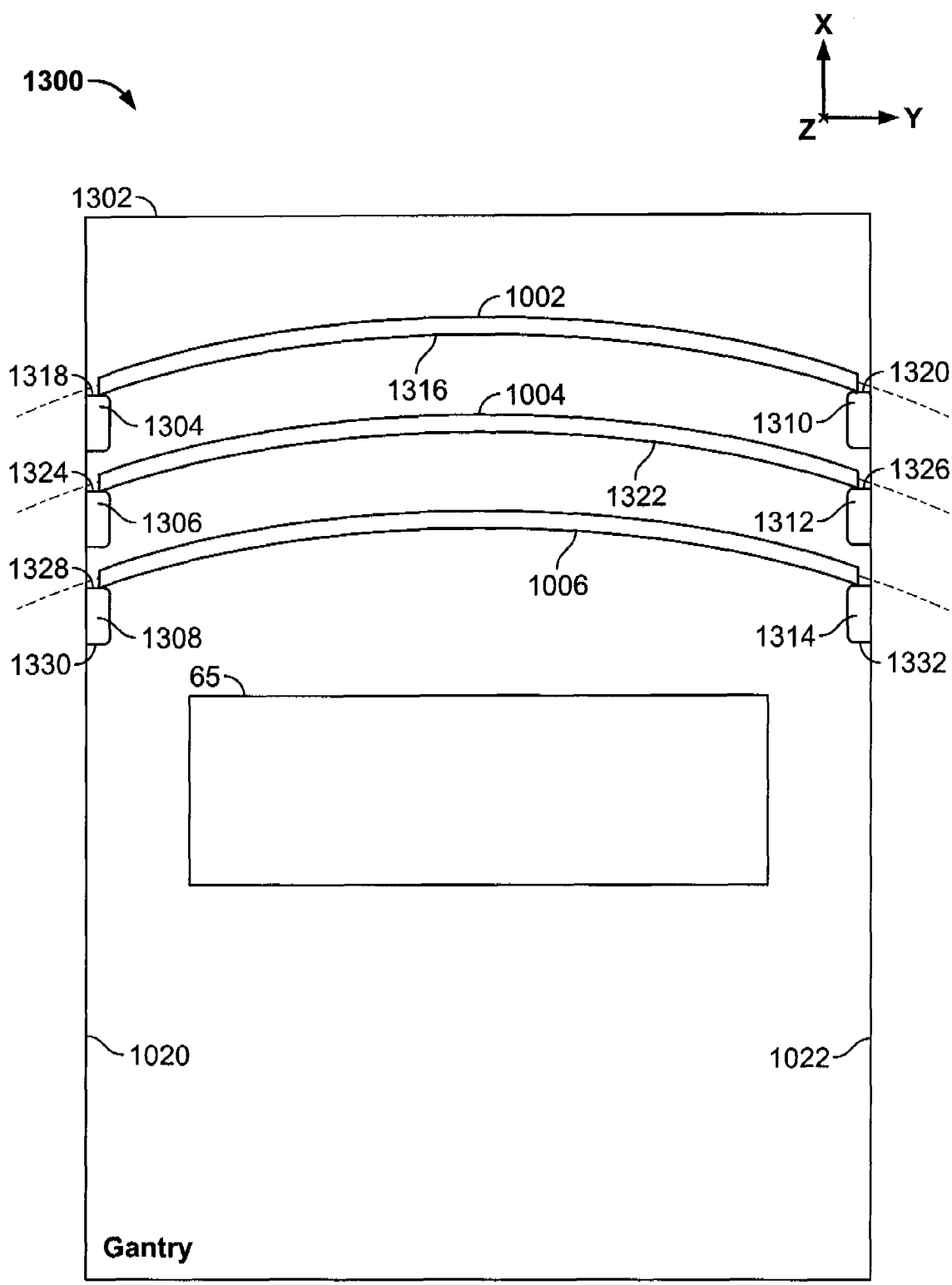
FIG. 27 is a diagram of an alternative embodiment of a gantry.

FIG. 27 is a diagram of an alternative embodiment of a gantry 1302. Gantry 1302 is an example of gantry 109 (FIG. 2). Gantry 1302 includes opening 65, a plurality of holders 1304, 1306, 1308, 1310, 1312, and 1314, and primary collimator elements 1002, 1004, and 1006. The user fabricates holders 1304, 1306, 1308, 1310, 1312, and 1314 from a metal, such as steel or aluminum. For example, the user fabricates holders 1304, 1306, 1308, 1310, 1312, and 1314 by using a molding machine including molds of a shape of any of holders 1304, 1306, 1308, 1310, 1312, and 1314, filling the molding machine with a liquid metal, such as steel, and cooling the liquid metal. The user attaches a primary collimator element to a plurality of top surfaces of holders by a process, such as spot welding or gluing, or alternatively by using screws. For example, the user attaches primary collimator element 1002 with holder 1304 by gluing a bottom surface 1316 of primary collimator element 1002 to a top surface 1318 of holder 1304 and gluing bottom surface 1316 of primary collimator element 1002 to a top surface 1320 of holder 1310. As another example, the user attaches primary collimator element 1004 with holder 1306 by spot welding a bottom surface 1322 of primary collimator element 1004 with a top surface 1324 of holder 1306 and spot welding bottom surface of primary collimator element 1004 with a top surface 1326 of holder 1312. Holders 1304, 1306, 1308, 1310, 1312, and 1314 do not include slots. Alternatively, the user attaches a top surface of a primary collimator element with a plurality of bottom surfaces of holders. For example, the user attaches a top surface 1328 of primary collimator element 1006 with a bottom surface 1330 of holder 1308 and a bottom surface 1332 of holder 1314.

Figure 28:
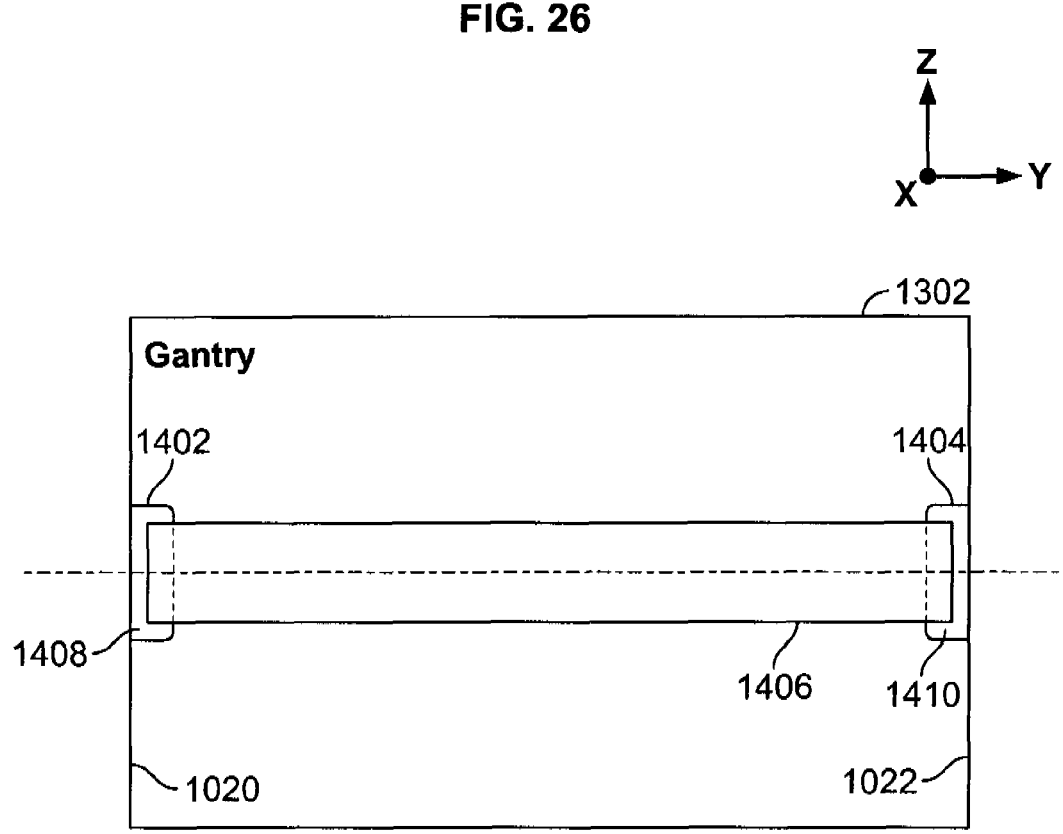
FIG. 28 is a top view of the gantry of FIG. 27.

FIG. 28 is a top view of an embodiment of gantry 1302. Gantry 1302 includes a plurality of holders 1402 and 1404, and a primary collimator element 1406. Primary collimator element 1406 is an example of any of primary collimator elements 1002, 1004, and 1006. Holders 1402 and 1404 are examples of holders 1304 and 1310, respectively, if primary collimator element 1406 is an example of primary collimator element 1002. Holders 1402 and 1404 are examples of holders 1306 and 1312, respectively, if primary collimator element 1406 is an example of primary collimator element 1004. Holders 1402 and 1404 are examples of holders 1308 and 1314, respectively, if primary collimator element 1406 is an example of primary collimator element 1006. Primary collimator element 1406 is attached to a top surface 1408 of holder and to a top surface 1410 of holder.

Figure 29:
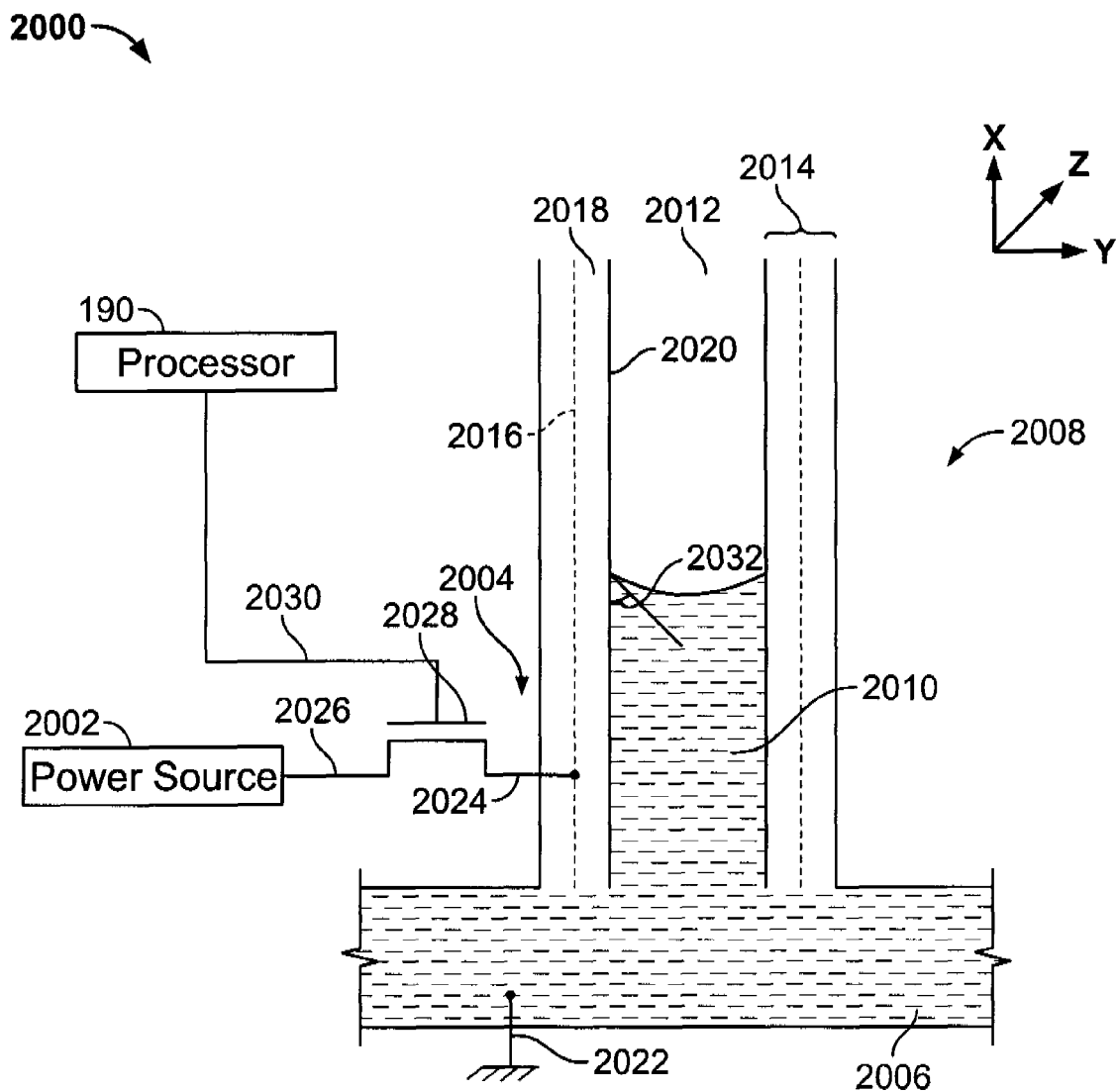
FIG. 29 is a block diagram of an embodiment of a filter element of the system of FIG. 2.

FIG. 29 is a block diagram of an embodiment of a system 2000 for identifying a substance. System 2000 includes processor 190, a power source 2002, a switching element 2004, which is a field effect transistor, a supply duct 2006, and a filter element 2008. An example of a power source 2002 includes a voltage source. Filter element 2008 is filled, via supply duct 2006, with a liquid filling 2010, which is electrically conductive and x-ray absorbing. Filter element 2008 includes an internal volume 2012 that is bounded by a plurality of walls 2014 of filter element 2008. Filter element 2008 includes a first electrode 2016 in the form of an electrically conductive layer, which is electrically isolated from liquid filling 2010 present in internal volume 2012 and the isolation is realized by an isolator layer 2018 and an inert cover layer 2020 that is provided on an inner side of walls 2014. Isolator layer 2018 and inert cover layer 2020 are included within filter element 2008. Filter element 2008 also includes a second electrode 2022 for applying an electric potential to liquid filling 2010. First electrode 2016 of filter element 2008 is coupled to switching element 2004 used to apply an electric voltage to filter element 2008. Switching element 2004 includes a drain contact 2024 and a source contact 2026 that is coupled to power source 2002. In an alternative embodiment, instead of switching element 2004, any other type of transistor, such as a bipolar junction transistor can be used. Switching element 2004 is activated or closed by a control voltage that is applied by processor 190 to a gate contact 2028 of switching element 2004 via a control line 2030. When switching element 2004 is closed, an electric voltage of power source 2002 is applied to first electrode 2016.

When switching element 2004 is closed and power source 2002 is set to a value of a "filling" voltage, such as ranging from and including 10 volts to 60 volts, a contact angle 2032 relative to inert cover layer 2020 decreases and filter element 2008 is filled with liquid filling 2010. The contact angle 2032 is an angle between inert cover layer 2020 and a tangent to liquid filling 2010 at a point of contact of liquid filling 2010 with inert cover layer 2020. When filter element 2008 is filled with liquid filling 2010, filter element 2008 is activated, liquid filling 2010 attenuates, such as absorbs, an x-ray beam, such as primary beam 84, and the x-ray beam does not pass through internal volume 2012 of filter element 2008. On the other hand, when processor 190 removes or does not apply the control voltage to gate contact 2028, switching element 2004 is open, and the electric voltage of power source 2002 is not applied to first electrode 2016, internal volume 2012 is not filled with liquid filling 2010. When internal volume 2012 is not filled with liquid filling 2010, filter element 2008 is deactivated and does not attenuate, such as absorb, an x-ray beam, such as primary beam 84 or primary beam 83, and the x-ray beam passes through internal volume 2012.

Figure 30:
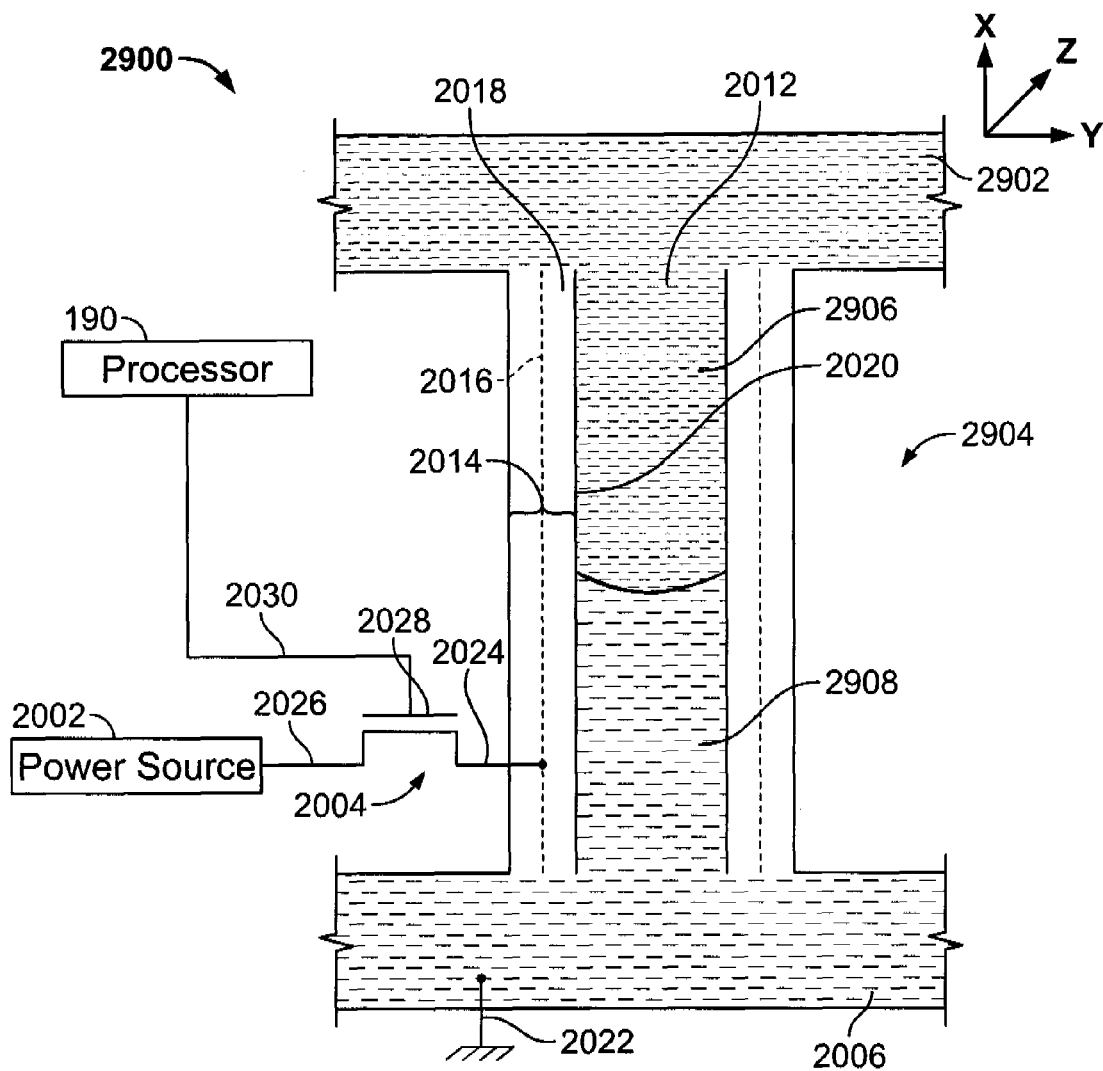
FIG. 30 is a block diagram of another embodiment of a filter element of the system of FIG. 2.

FIG. 30 is a block diagram of an alternative embodiment of a system 2900 for identifying a substance. System 2900 includes power source 2002, processor 190, switching element 2004, supply duct 2006, a supply duct 2902, and a filter element 2904. Filter element 2904 is filled with a liquid filling that includes an electrically conductive liquid component 2906, which does not absorb x-rays, and an x-ray absorbing liquid component 2908. Liquid components 2906 and 2908 are not miscible. Respective liquid components 2906 and 2908 are applied via respective supply ducts 2902 and 2006, respectively. The other functional parts of filter element 2904 are similar to those of the filter element 2008.

When processor 190 applies the control voltage to switching element 2004, switching element 2004 closes and internal volume 2012 is filled within x-ray absorbing liquid component 2908 and not filled with electrically conductive liquid component 2906. When internal volume 2012 is filled with x-ray absorbing liquid component 2908, filter element 2904 is activated and attenuates an x-ray beam, such as primary beam 84, and the x-ray beam is attenuated, such as does not pass through, internal volume 2012. On the other hand, when internal volume 2012 is filled with electrically conductive liquid component 2906, filter element 2904 is deactivated and does not attenuate an x-ray beam, such as primary beam 84, and the x-ray beam is not attenuated, such as passes through, internal volume 2012.

Figure 31:
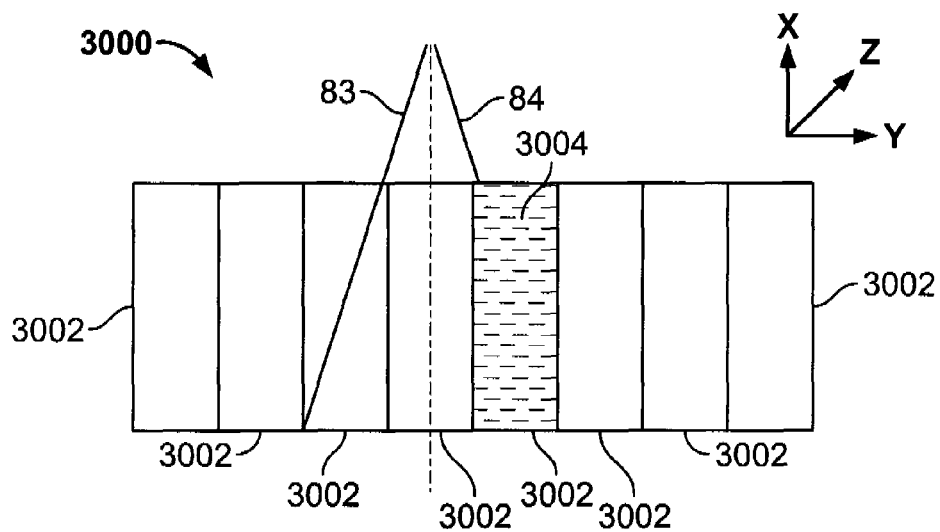
FIG. 31 is a block diagram of an embodiment of a filter of the system of FIG. 2.

FIG. 31 is a block diagram of an embodiment of a filter 3000 for identifying a substance. Filter 3000 operates according to an electrowetting process. Filter 3000 includes a plurality of filter elements 3002. Each filter element 3002 is an example of either filter element 2008 (FIG. 29) or filter element 2904 (FIG. 30). Filter 3000 is an example of beam selector 111 (FIG. 2). When filter element 3002 is filled with a liquid filling 3004, which is an example of either liquid filling 2010 or x-ray absorbing liquid component 2908, filter element 3002 is activated and an x-ray beam, such as primary beam 84, passing through filter element 3002 is attenuated by filter element 3002. On the other hand, when filter element 3002 is not filled with liquid filling 3004, filter element 3002 is deactivated and an x-ray beam, such as primary beam 84 or primary beam 83, is not attenuated by filter element 3002. Processor 190 controls each filter element 3002 individually via switching element 2004. For example, processor 190 activates filter element 3002 via switching element 2004 and activates another filter element, such as filter element 3002, via another switching element, such as switching element 2004.

Technical effects of the herein described systems and methods for identifying a substance identifying substance 82. Substance 82 is identified by comparing the effective atomic numbers $Z_{Aeff}$ and $Z_{Beff}$ with each other and comparing parameters, such as the diffraction profile $D_A(m)$, the effective atomic number $Z_{Aeff}$, the packing fraction $\eta_A$, the diffraction profile $D_B(m)$, the effective atomic number $Z_{Beff}$, the packing fraction $\eta_B$, with the listed parameters in the table.

While the invention has been described in terms of various specific embodiments, those skilled in the art will recognize that the invention can be practiced with modification within the spirit and scope of the claims.

What is claimed is:

1. A method for identifying a substance, said method comprising:
   detecting, by a first scatter detector, a first set of scattered radiation;
   generating a first effective atomic number from the first set of scattered radiation;
   detecting, by a second scatter detector, a second set of scattered radiation;
   generating a second effective atomic number from the second set of scattered radiation; and
   determining whether the first effective atomic number is within a limit of the second effective atomic number.

2. A method in accordance with claim 1 further comprising:
   storing the first and second effective atomic numbers upon determining that the first effective atomic number is within the limit of the second effective atomic number; and generating a packing fraction from the second set of scattered radiation upon determining that the first effective atomic number is not within the limit of the second effective atomic number.

3. A method in accordance with claim 1 further comprising:
generating a first diffraction profile from the first set of scattered radiation;
generating a first packing fraction from the first effective atomic number; and
determining whether at least one of the first packing fraction, the first effective atomic number, and the first diffraction profile is within a threshold of at least one of a plurality of parameters of a set stored in a memory device.

4. A method in accordance with claim 1, wherein the first effective atomic number is not generated from the second set of scattered radiation.

5. A method in accordance with claim 1, wherein the second effective atomic number is not generated from the first set of scattered radiation.

6. A method in accordance with claim 1 further comprising:
generating a first diffraction profile from the first set of scattered radiation;
generating a first packing fraction from the first effective atomic number;
determining whether at least one of the first packing fraction, the first effective atomic number, and the first diffraction profile is within a threshold of at least one of a plurality of parameters of a set stored in a memory device; and
determining the substance as identified upon determining that at least one of the first packing fraction, the first effective atomic number, and the first diffraction profile is within the threshold.

7. A method in accordance with claim 1 further comprising:
generating a first diffraction profile from the first set of scattered radiation;
generating a first packing fraction from the first effective atomic number;
determining whether at least one of the first packing fraction, the first effective atomic number, and the first diffraction profile is within a threshold of at least one of a plurality of parameters of a set stored in a memory device, wherein said determining whether the first effective atomic number is within a limit of the second effective atomic number comprises determining whether the first effective atomic number is within the limit of the second effective atomic number upon determining that at least one of the first packing fraction, the first effective atomic number, and the first diffraction profile is not within the threshold.

8. A method in accordance with claim 1 further comprising generating a packing fraction from the second effective atomic number upon determining that the first effective atomic number is not within the limit of the second effective atomic number.

9. A method in accordance with claim 1 further comprising:
generating a packing fraction from the second effective atomic number upon determining that the first effective atomic number is not within the limit of the second effective atomic number; and
determining whether at least one of the second effective atomic number, the packing fraction, and a second diffraction profile is within a scope of at least one of a plurality of listed parameters within a set, wherein the second diffraction profile is generated from the second set of scattered radiation.

10. A method in accordance with claim 1 further comprising:
generating a packing fraction from the second effective atomic number upon determining that the first effective atomic number is not within the limit of the second effective atomic number;
determining whether at least one of the second effective atomic number, the packing fraction, and a second diffraction profile is within a scope of at least one of a plurality of listed parameters within a set; and
determining the substance as identified upon determining that at least one of the second effective atomic number, the packing fraction, and the second diffraction profile are within the scope of the at least one of the plurality of listed parameters.

11. A method in accordance with claim 1 further comprising:
generating a packing fraction from the second effective atomic number upon determining that the first effective atomic number is not within the limit of the second effective atomic number;
determining whether at least one of the second effective atomic number, the packing fraction, and a second diffraction profile is within a scope of at least one of a plurality of listed parameters within a set; and
storing the second diffraction profile, the second effective atomic number, the packing fraction, and the first effective atomic number upon determining that at least one of the second effective atomic number, the packing fraction, and the second diffraction profile is not within the scope.

12. A system for identifying a substance, said system comprising:
a first scatter detector configured to detect a first set of scattered radiation;
a second scatter detector configured to detect a second set of scattered radiation; and
a processor configured to generate a first effective atomic number from the first set of scattered radiation, to generate a second effective atomic number from the second set of scattered radiation, and to determine whether the first effective atomic number is within a limit of the second effective atomic number.

13. A system in accordance with claim 12, wherein said processor further configured to:
store the first and second effective atomic numbers upon determining that the first effective atomic number is within the limit of the second effective atomic number; and
generate a packing fraction from the second set of scattered radiation upon determining that the first effective atomic number is not within the limit of the second effective atomic number.

14. A system in accordance with claim 12, wherein said processor further configured to:
generate a first diffraction profile from the first set of scattered radiation;
generate a first packing fraction from the first effective atomic number; and
determine whether at least one of the first packing fraction, the first effective atomic number, and the first diffraction profile is within a threshold of at least one of a plurality of parameters of a set stored in a memory device.

15. A system in accordance with claim 12, wherein the first effective atomic number is not generated from the second set of scattered radiation.

16. A system in accordance with claim 12, wherein the second effective atomic number is not generated from the first set of scattered radiation.

17. A system for identifying a substance, said system comprising:
- a plurality of x-ray sources configured to generate x-rays;
- a first scatter detector configured to detect a first set of scattered radiation generated from the x-rays;
- a second scatter detector configured to detect a second set of scattered radiation;
- a processor configured to generate a first effective atomic number from the first set of scattered radiation, to generate a second effective atomic number from the second set of scattered radiation, and to determine whether the first effective atomic number is within a limit of the second effective atomic number; and
- a plurality of switches configured to couple said processor to the first set of scattered radiation when decoupling said processor from the second set of scattered radiation.

18. A system in accordance with claim 17, wherein said processor further configured to:
- store the first and second effective atomic numbers upon determining that the first effective atomic number is within the limit of the second effective atomic number; and
- generate a packing fraction from the second set of scattered radiation upon determining that the first effective atomic number is not within the limit of the second effective atomic number.

19. A system in accordance with claim 17, wherein said processor further configured to:
- generate a first diffraction profile from the first set of scattered radiation;
- generate a first packing fraction from the first effective atomic number; and
- determine whether at least one of the first packing fraction, the first effective atomic number, and the first diffraction profile is within a threshold of at least one of a plurality of parameters of a set stored in a memory device.

* * * * *